US009388420B2

(12) United States Patent
Kore et al.

(10) Patent No.: US 9,388,420 B2
(45) Date of Patent: Jul. 12, 2016

(54) ALKYNYL-DERIVATIZED CAP ANALOGS, PREPARATION AND USES THEREOF

(71) Applicant: LIFE TECHNOLOGIES CORPORATION, Carlsbad, CA (US)

(72) Inventors: Anilkumar Kore, Austin, TX (US); Shanmugasundaram Muthian, Austin, TX (US); Kyle Gee, Springfield, OR (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 14/600,155

(22) Filed: Jan. 20, 2015

(65) Prior Publication Data
US 2015/0252373 A1    Sep. 10, 2015

Related U.S. Application Data

(62) Division of application No. 13/655,103, filed on Oct. 18, 2012, now Pat. No. 8,969,545.

(60) Provisional application No. 61/548,653, filed on Oct. 18, 2011.

(51) Int. Cl.
| *A01N 43/04* | (2006.01) |
| *A61K 31/70* | (2006.01) |
| *C12N 15/67* | (2006.01) |
| *A61K 31/7088* | (2006.01) |
| *A61K 31/7084* | (2006.01) |
| *A61K 31/7115* | (2006.01) |
| *A61K 31/712* | (2006.01) |
| *C07C 247/04* | (2006.01) |
| *C07D 213/82* | (2006.01) |
| *C07H 19/207* | (2006.01) |
| *C07H 21/02* | (2006.01) |
| *C12Q 1/68* | (2006.01) |
| *C12N 15/11* | (2006.01) |
| *A61K 48/00* | (2006.01) |

(52) U.S. Cl.
CPC ............ *C12N 15/67* (2013.01); *A61K 31/7084* (2013.01); *A61K 31/7088* (2013.01); *A61K 31/712* (2013.01); *A61K 31/7115* (2013.01); *C07C 247/04* (2013.01); *C07D 213/82* (2013.01); *C07H 19/207* (2013.01); *C07H 21/02* (2013.01); *C12N 15/11* (2013.01); *C12Q 1/68* (2013.01); *A61K 48/00* (2013.01)

(58) Field of Classification Search
None
See application file for complete search history.

(56) References Cited

U.S. PATENT DOCUMENTS

| 7,375,234 B2 | 5/2008 | Sharpless et al. |
| 7,572,908 B2 | 8/2009 | Dellinger et al. |
| 7,763,736 B2 | 7/2010 | Sharpless |
| 2005/0222427 A1 | 10/2005 | Sharpless et al. |
| 2010/0261231 A1 | 10/2010 | Kore et al. |

FOREIGN PATENT DOCUMENTS

| WO | WO-03/101972 | 12/2003 |
| WO | WO-2008/016473 | 2/2008 |
| WO | WO-2009/058911 | 5/2009 |

OTHER PUBLICATIONS

Yan et al. RNA (2005), vol. 11, pp. 1238-1244.*
"PCT/US2012/060832 International Search Report and Written Opinion mailed".
Heiser, Axel et al., "Autologous dendritic cells transfected with prostate-specific antigen RNA stimulate CTL responses against metastatic prostate tumors", *J. Clin. Invest.*, vol. 109, No. 3, 2002, 409-417.
Kolb, H. C. et al., "Click Chemistry: Diverse Chemical Function from a Few Good Reactions", *Angewandte Chemie International Edition in English*, 40, 2001, 2004-2021.
Lewis, W. G. et al., "Click chemistry in Situ: Acetylcholinesterase as a Reaction Vessel for the Selectivity Assembly of a Femtomolar Inhibitor from an Array of building Blocks", *Angewandte Chemie International Edition in English*, 41(6), 2002, 1053-1057.
Morse, Michael A. et al., "The Feasibility and Safety of Immunotherapy with Dendritic Cells Loaded with CEA mRNA Following Neoadjuvant Chemoradiotherapy and Resection of Pancreatic Cancer", *International Journal of Gastrointestinal Cancer*, vol. 32, No. 1, 2002, 1-6.
Steinman, Ralph M. et al., "Taking dendritic cells into medicine", *Nature*, vol. 449, 2007, 419-426.
Volpi, E. et al., "Exogenous Amino Acids Stimulate Net Muscle Protein Synthesis in the Elderly", *The American Society for Clinical Investigation, Inc.*, vol. 101, 1998, pp. 2000-2007.

* cited by examiner

Primary Examiner — Patrick Lewis

(57) ABSTRACT

Alkynyl-derivatized cap analogs, alkynyl-modified capped RNA, 1,4-disubstituted triazole-derivatized capped RNA, methods of preparation, methods of isolation, and uses thereof are provided. The "click" modification facilitates detection and isolation of capped RNAs and the 1,4-disubstituted triazole derivatives formed by the "click" reaction are useful for producing RNA transcripts and encoded protein.

4 Claims, 12 Drawing Sheets

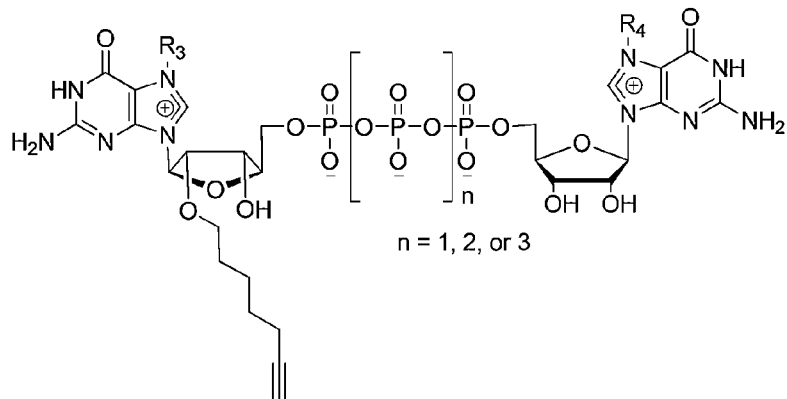
FIG. 1E
FIG. 1F
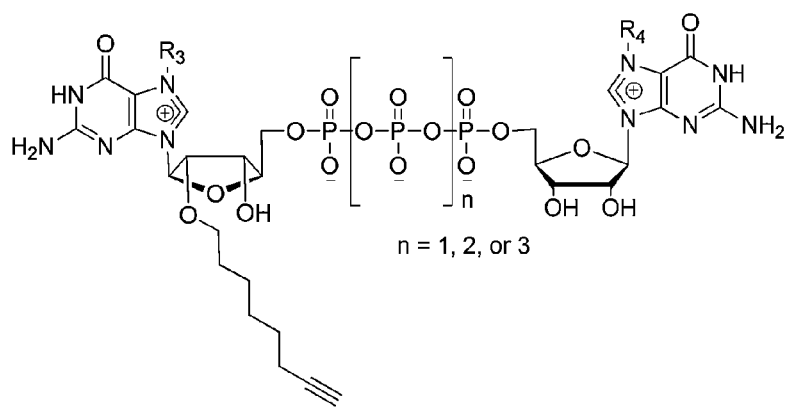
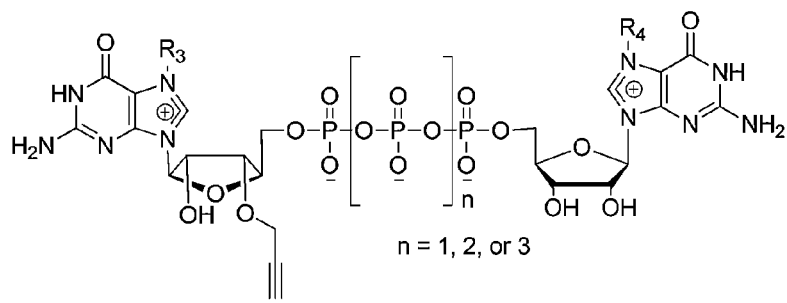
FIG. 1G
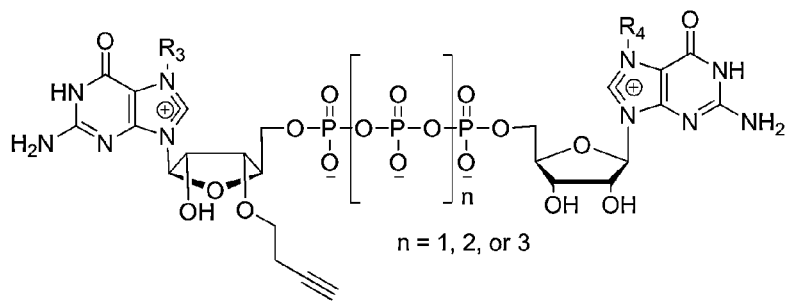
FIG. 1H

SEQUENCE LISTING

```
<160> NUMBER OF SEQ ID NOS: 1

<210> SEQ ID NO 1
<211> LENGTH: 10
<212> TYPE: RNA
<213> ORGANISM: Unknown
<220> FEATURE:
<223> OTHER INFORMATION: Description of Unknown:
      Kozak consensus sequence

<400> SEQUENCE: 1
gccaccaugg                                                          10
```

US 9,388,420 B2

ALKYNYL-DERIVATIZED CAP ANALOGS, PREPARATION AND USES THEREOF

RELATED APPLICATION

This application is a Division of U.S. application Ser.No. 13/655,103, filed on Oct. 18, 2012, which claims the benefit of U.S. Provisional Application No. 61/548,653, filed Oct. 18, 2011, the disclosure of which is specifically incorporated herein by reference in its entirety.

SEQUENCE LISTING

The instant application contains a Sequence Listing which has been submitted electronically in ASCII format and is hereby incorporated by reference in its entirety. Said ASCII copy, created on Apr. 16, 2015, is named LT00589DIV_SL.txt and is 588 bytes in size.

FIELD

This specification generally relates to RNA cap analogs, methods of use and kits. In particular, cap analogs provided herein permit ready detection and/or isolation of capped RNA transcripts in vitro and translation of capped mRNAs in vivo.

BACKGROUND

Eukaryotic mRNAs bear a "cap" structure at their 5'-termini that is well known to play an important role in translation. Naturally occurring cap structures consist of a 7-methyl guanosine that is linked via a triphosphate bridge to the 5'-end of the first transcribed nucleotide, resulting in $m^7G(5')ppp(5')$ N, where N is any nucleotide. The mRNA cap plays an important role in gene expression. It protects the mRNAs from degradation by exonucleases, enables transport of RNAs from the nucleus to the cytoplasm, and participates in assembly of the translation initiation complex. $m^7G(5')ppp(5')G$ (mCAP) has been used as the primer in transcription with T7 or SP6 RNA polymerase in vitro to obtain RNAs having a cap structure in their 5'-termini. In vivo, the cap is added enzymatically. However, over the past 20 years or so, numerous studies have required the synthesis of proteins in an in vitro translation extract supplemented with in vitro synthesized mRNA. The prevailing method for the in vitro synthesis of capped mRNA employs a pre-formed dinucleotide of the form $m^7G(5')ppp(5')G$ as an initiator of transcription. A disadvantage of using mCAP, a pseudosymmetrical dinucleotide, has always been the propensity of the 3'-OH of either the G or $m^7G$ ($m^7Guo$) moiety to serve as the initiating nucleophile for transcriptional elongation. This disadvantage was addressed by provision of modified cap analogs having the 3'-OH group of the $m^7G$ portion of the cap blocked to prevent transcription from that position.

In the cell, the cap is added in the nucleus and is catalyzed by the enzyme guanylyl transferase. The addition of the cap to the 5' terminal end of RNA occurs after transcription but immediately after transcription initiation so that it is almost impossible to detect. The terminal nucleoside is always a guanine, and is in the reverse orientation to all the other nucleotides, i.e., 5'Gppp5'GpNpNp . . . and the cap contains two nucleotides, connected by a 5'-5' triphosphate linkage.

Transcription of RNA usually starts with a nucleoside triphosphate (usually a purine, A or G). When transcription occurs in vitro, it typically includes a phage RNA polymerase such as T7, T3 or SP6, a DNA template containing a phage polymerase promoter, nucleotides (ATP, GTP, CTP and UTP) and a buffer containing magnesium salt. The 5' cap structure enhances the translation of mRNA by helping to bind the eukaryotic ribosome and assuring recognition of the proper AUG initiator codon. This function may vary with the translation system and with the specific mRNA being synthesized.

During translation the cap is bound by translation initiation factor eIF4E and the cap-binding complex (CBC) recruits additional initiation factors. Decapping is catalyzed by proteins dcp1 and dcp2 which compete with eIF4E to bind to the cap. Translation results in amino acids as encoded by the mRNA to join together to form a peptide and occurs as three processes, initiation, elongation and termination. Initiation in eukaryotes involves attachment of a ribosome which scans the mRNA for the first methionine codon. Elongation proceeds with the successive addition of amino acids until a stop codon is reached, terminating translation.

Capped RNA encoding specific genes can be transfected into eukaryotic cells or microinjected into cells or embryos to study the effect of translated product in the cell or embryo. If uncapped RNA is used, the RNA in these experiments is rapidly degraded and the yield of translated protein is much reduced.

Capped RNA can also be used to treat disease. Isolated dendritic cells from a patient can be transfected with capped RNA encoding immunogen. The dendritic cells translate the capped RNA into a protein that induces an immune response against this protein. In a small human study, immunotherapy with dendritic cells loaded with CEA capped RNA was shown to be safe and feasible for pancreatic patients (Morse et al., *Int. J. Gastroinstest. Cancer,* 32, 1-6, (2002)). It was also noted that introducing a single capped RNA species into immature dendritic cells induced a specific T-cell response (Heiser et al., *J. Clin. Invest.,* 109, 409-417 (2002)).

Thus, there is a need for mRNA cap analogs to produce capped mRNA in vitro.

SUMMARY

Aspects of the present disclosure include a composition comprising an alkynyl-derivatized cap analog having the structure: $R_3^{7,3'-O-alkynyl}G[5']p[p]_np[5']G$, $R_3^{7,3'-O-alkynyl}G[5']p[p]_np[5']A$, $R_3^{7,2'-O-alkynyl}G[5']p[p]_np[5']G$, $R_3^{7,2'-O-alkynyl}G[5']p[p]_np[5']A$, or a salt thereof; wherein $R_3$ is alkyl or arylalkyl; the alkynyl moiety comprises 3-24 carbon atoms, a terminal alkyne, and is optionally substituted; n is 1, 2, or 3; A is adenosine; and G is guanosine. Further embodiments of the disclosure include a composition comprising RNA having such a cap analog covalently bonded thereto.

In certain embodiments, the alkynyl-derivatized cap analog comprises the structure: $m^{7,3'-O-alkynyl}G[5']ppp[5']G$, $m^{7,3'-O-alkynyl}G[5']ppp[5']A$, $m^{7,2'-O-alkynyl}G[5']ppp[5']G$, $m^{7,2'-O-alkynyl}G[5']ppp[5']A$, or a salt thereof, wherein the alkynyl moiety comprises a terminal alkyne and comprises 3-8 carbon atoms, A is adenosine, and G is guanosine. Further aspects include a composition comprising such a compound and a physiologically acceptable carrier, or a composition comprising such a compound covalently bonded to RNA.

Other embodiments of the present disclosure include a composition comprising an alkynyl-derivatized cap analog having the structure:

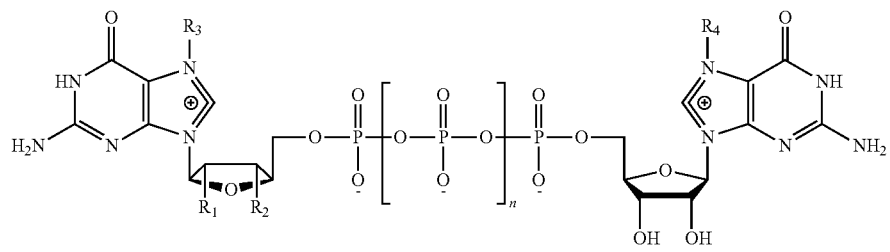

n = 1, 2, or 3 or a salt thereof, wherein at least one of $R_1$ and $R_2$ comprises $O(CH_2)_mC{\equiv}CH$ and m is 1 to 6, and the other of $R_1$ and $R_2$ comprises OH or H; $R_3$ is alkyl or arylalkyl; and $R_4$ is absent, H, alkyl or arylalkyl. In an embodiment of the composition, $R_2$ comprises $O(CH_2)_mC{\equiv}CH$ and m is 1 to 6, and $R_1$ comprises OH. In another embodiment of the composition, $R_1$ comprises $O(CH_2)_mC{\equiv}CH$ and m is 1 to 6, and $R_2$ comprises OH. In aspects of the disclosure, n is 1. In aspects of the disclosure, m is 1. The alkyne group of $R_1$ or $R_2$ is a terminal alkyne.

Such alkynyl-derivatized cap analogs are anti-reverse cap analogs since at least one of $R_1$ and $R_2$ is derivatized. This modification forces RNA polymerases to initiate transcription with the remaining —OH group in the G residue of the cap and thus synthesize RNA transcripts capped exclusively in the correct orientation. Therefore, use of the cap analog provided herein allows for synthesis of capped RNAs that are 100% functional in contrast to transcription reactions using traditional cap analogs where only half of the cap analog is incorporated in the correct orientation.

In some embodiments, compositions are provided comprising:

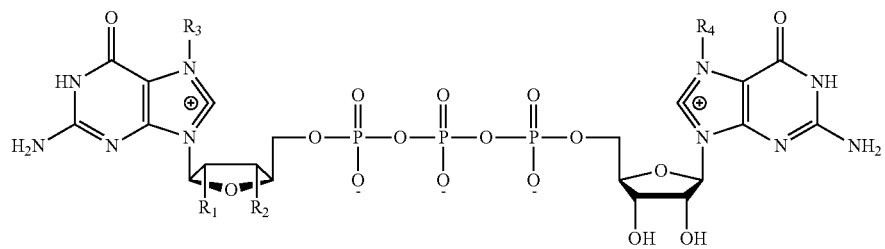

or a salt thereof, wherein at least one of $R_1$ and $R_2$ comprises $O(CH_2)_mC{\equiv}CH$ and m is 1 to 6, and the other of $R_1$ and $R_2$ comprises OH or H; $R_3$ is alkyl or arylalkyl; and $R_4$ is absent, H, alkyl or arylalkyl.

A further embodiment includes a method of synthesizing an alkynyl-derivatized cap analog comprises combining a 2'- or a 3'-alkynyl-derivatized m7G diphosphate with imidazole-derivatized GMP under conditions and for a time to produce an alkynyl-derivatized cap analog.

An aspect of the present disclosure is a method of producing 5'-alkynyl-modified capped RNA comprising contacting a nucleic acid substrate with a RNA polymerase and an alkynyl-derivatized cap analog as described herein in the presence of nucleotide triphosphates under conditions and for a time to produce 5'-alkynyl-modified capped RNA. 5'-Alkynyl-derivatized capped mRNAs are used for protein synthesis in reticulocyte lysates, wheat germ lysates, and other in vitro systems, for example.

Isolation and/or detection of such a capped RNA is achieved by a method comprising contacting the alkynyl-modified capped RNA with an azide-derivatized moiety to form a 1,4-disubstituted triazole-derivatized capped RNA. In an embodiment, the azide-derivatized moiety comprises a detectable moiety and the detectable moiety comprises a reporter molecule, biotin, or a peptide.

In one embodiment, a method comprises contacting a 1,4-disubstituted triazole-derivatized capped RNA with a solid support having binding affinity and specificity for the detectable moiety. When the detectable moiety comprises biotin and the solid support comprising avidin or streptavidin, for example, detection and/or isolation is achieved.

An aspect of the disclosure is a method of separating 5'-alkynyl-modified capped RNA from uncapped RNA in a sample, comprising contacting the sample with a solid support having an azide-derivatized cleavable linker bound thereto under conditions and for a time to produce a 1,4-disubstituted triazole-derivatized capped RNA-solid support conjugate; separating the conjugate from uncapped RNA; and, cleaving the 1,4-disubstituted triazole-derivatized capped RNA from the solid support, thereby separating the alkynyl-modified capped RNA from uncapped RNA. In some embodiments, the method includes a step of filtration and/or ethanol precipitation. In some embodiments, the cleavable linker comprises a disulfide linkage.

Aspects of a solid support for use in the present disclosure include compositions comprising a solid support having a cleavable linker attached thereto and having a terminal azido group for use in "click" chemical reactions. Such compositions, in some embodiments, comprise, for example,

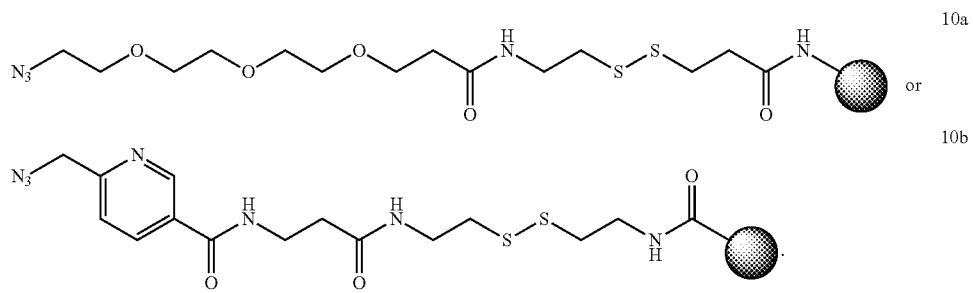

Further embodiments of the present disclosure include a kit for capping an RNA transcript comprising an alkynyl-derivatized cap analog as described herein; nucleotide triphosphate molecules; and a RNA polymerase. Such kits may further include an azide-derivatized solid support, a ribonuclease inhibitor, or a polymerase buffer, for example.

1,4-Disubstituted triazole-derivatized capped RNA can be microinjected or transfected into cells or organisms for in vivo studies. Accordingly, as aspect of the disclosure is a biological cell comprising a 1,4-disubstituted triazole-derivatized capped RNA.

In a further aspect of the disclosure, a method of introducing an exogenous protein into a subject is provided, the method comprising transfecting the subject with a 1,4-disubstituted triazole-derivatized capped mRNA encoding the exogenous protein; and allowing intracellular translation to produce the exogenous protein. In an embodiment in which the subject is responsive to immunotherapy, the exogenous protein may be an immunogen. In the case where the subject is a cell, the cell may be an antigen presenting cell (APC).

Other aspects include a method for treatment of disease of a subject, comprising providing to the subject one or more mRNAs comprising a 1,4-disubstituted triazole-derivatized cap analog wherein the mRNA encodes a protein that treats the disease. In some embodiments, the mRNA comprising a 1,4-disubstituted triazole-derivatized cap analog is contained within a cell and the cell is an antigen presenting cell (APC). In some embodiments, the APC is a dendritic cell, a macrophage, a B cell or a T cell. In some embodiments, the mRNAs comprising a 1,4-disubstituted triazole-derivatized cap analog is introduced into the cell by transfection.

Cap analogs and capped RNA as provided herein are also useful for RNA splicing and for situations in which the stability of RNA is a factor.

BRIEF DESCRIPTION OF THE DRAWINGS

The skilled artisan will understand that the drawings, described below, are for illustration purposes only. The drawings are not intended to limit the scope of the present teachings in any way.

FIG. 1A-FIG. 1L provide structures of alkynyl-modified cap analogs. FIG. 1A-FIG. 1F depict 2'-modified structures while FIG. 1G-FIG. 1L depict 3'-modified structures.

FIG. 5A provides a reaction scheme for coupling mRNA 7a bearing alkynyl cap analog 7 with azide-derivatized solid-support 10a to form reaction product 11a, which reaction product is cleaved by DTT to provide capped mRNA 12a.

FIG. 6 provides data on the translational efficiency of mRNA for luciferase, the mRNA containing a mixture of standard capped mRNA and alkynyl-modified capped mRNA 7a.

DETAILED DESCRIPTION

Figure 1A:
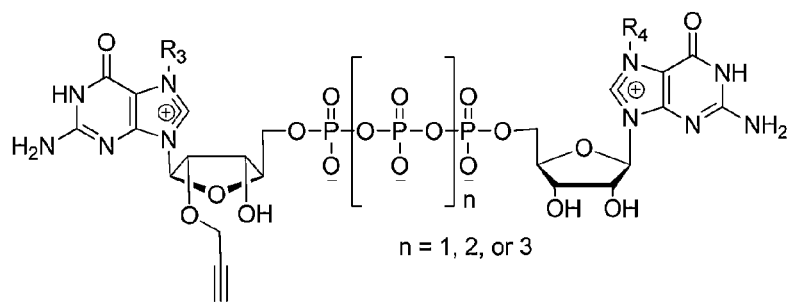
Figure 1B:
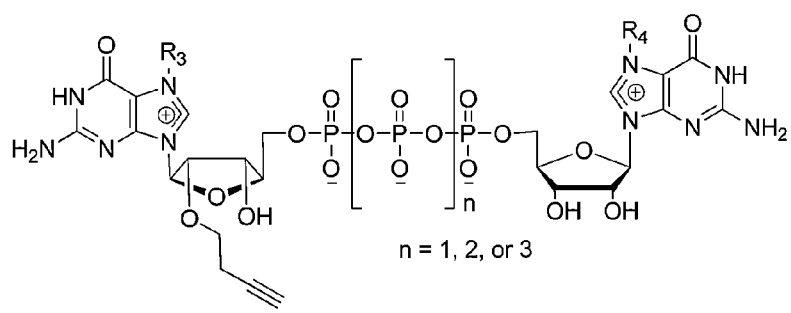
Figure 1C:
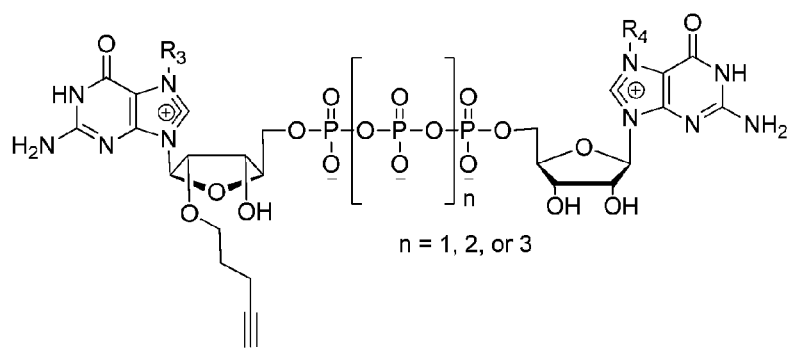
Figure 1D:
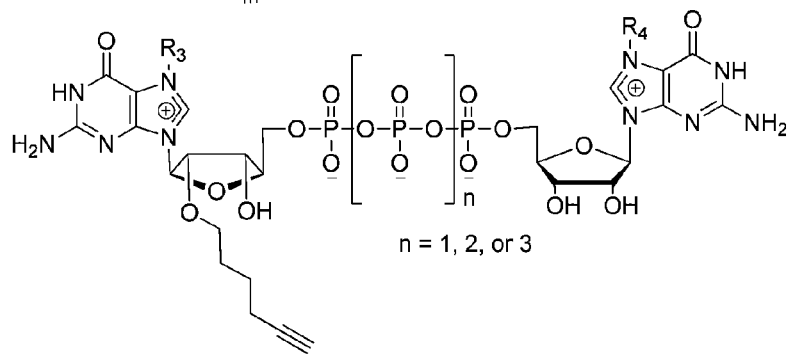
Figure 1I:
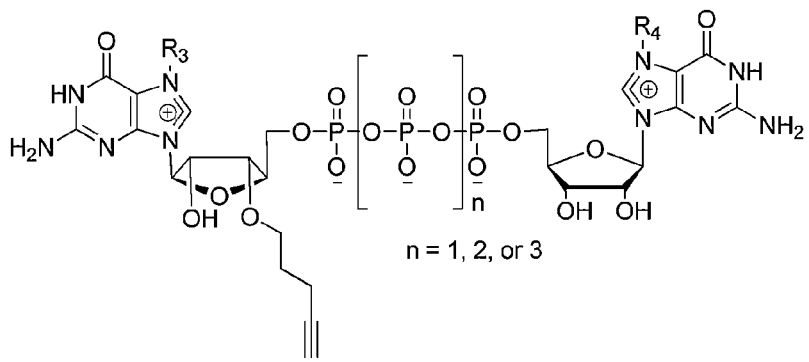
Figure 1J:
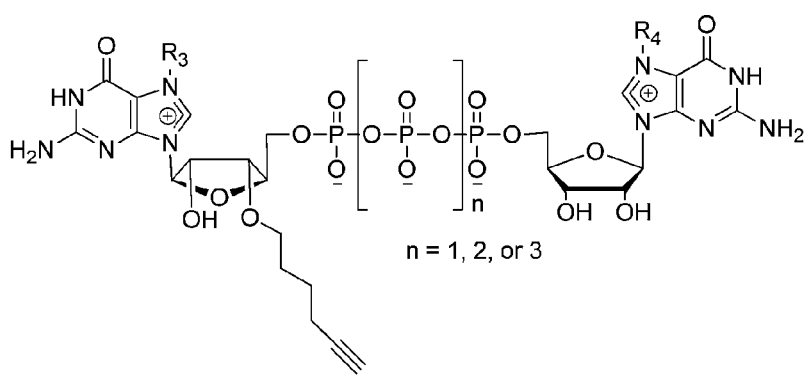
Figure 1K:
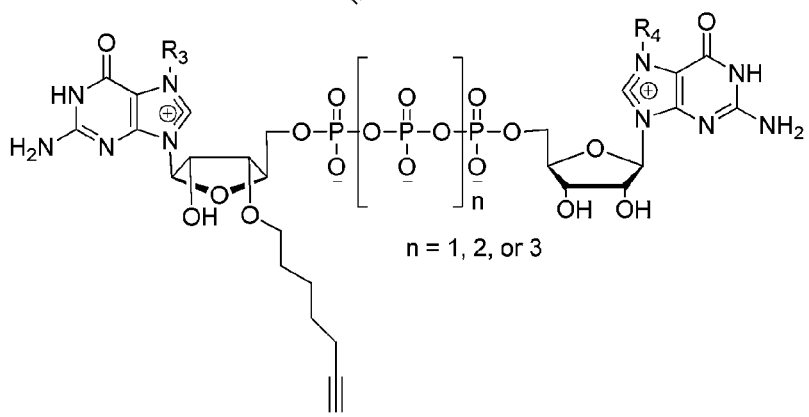
Figure 1L:
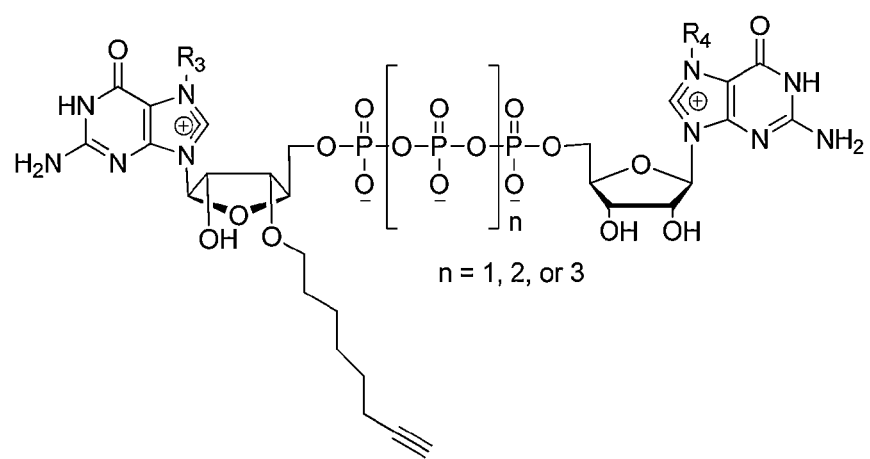

The present application provides methods and compositions related to cap analogs for use in transcription, for use in detection and isolation of capped RNA, for use of resultant isolated RNA in translation both in vitro and in vivo. Also included are methods of using the resultant isolated RNA in research and treatment of disease. The alkynyl-derivatized cap analogs provided herein have the advantage of only being incorporated in transcription capping reactions in the forward direction.

In the examples provided below, the effect of the 3'-O-propargyl substitution on the cap analog has been evaluated with respect to its in vitro transcription by using T7 RNA polymerase, capping efficiency and translational activity. The gel shift assay indicated that the standard cap analog, m7GppG has a capping efficiency of 73% and the alkynyl-modified cap has a capping efficiency of 60%. The capping efficiency experiment clearly demonstrated that the alkynyl-modified cap analog was a substrate for T7 RNA polymerase. The results in the examples show that the mRNA poly(A) capped with 3'-O-propargyl substituted cap analog (the alkynyl-modified cap analog) was translated 3.1 fold more efficiently than the mRNA capped with the standard cap analog (m7GppG). The examples also provide methods for using solid-supported "click" chemistry to isolate mRNA that is 100% capped (e.g., contains no uncapped mRNA).

In an embodiment, alkynyl-derivatized capped RNA is detected and/or isolated using "click" technology in which a copper-catalyzed covalent reaction is used to attach the capped RNA to an azide-derivatized reporter moiety to form a 1,4-disubstituted triazole-derivatized capped RNA-reporter conjugate. The reporter moiety can be used to detect and/or isolate the capped mRNA from uncapped mRNA.

In another embodiment, alkynyl-derivatized capped RNA is isolated using "click" technology in which a copper-catalyzed covalent reaction is used to attach the capped RNA to an azide-derivatized solid support to form a 1,4-disubstituted triazole-derivatized capped RNA-solid support conjugate. This allows for isolation of capped mRNA from uncapped RNA. Subsequent cleavage from the solid support, for example, when the alkynyl group or the azide moiety contains a cleavable linker, yields derivatized RNA that can be separated from the solid support.

The use of "or" means "and/or" unless stated otherwise or where the use of "and/or" is clearly inappropriate. The use of "a" means "one or more" unless stated otherwise or where the use of "one or more" is clearly inappropriate. The use of "comprise," "comprises," "comprising," "include," "includes," and "including" are interchangeable and not intended to be limiting.

are used for protein synthesis in reticulocyte lysates, wheat germ lysates, and other in vitro systems, or can be microinjected or transfected into cells or organisms for in vivo studies. They can also be used in RNA splicing and stability studies.

An alkynyl-derivatized cap analog refers to an extendible di-nucleotide cap, containing an alkynyl group at a 2' or 3' position, that facilitates transcription of a template, translation of a transcript, and/or confers stability to an RNA transcript. The cap analog is incorporated at the 5' end of an RNA transcript. Examples of alkynyl-derivatized cap analogs are provided by FIG. 1A-FIG. 1L in which an alkynyl moiety is attached at the 3' or 2' position on the ribose ring as designated, for example, by the structure: $R_3^{7,3'\text{-}O\text{-}alkynyl}G[5']p[p]_np[5']R_4^7G$, or $R_3^{7,2'\text{-}O\text{-}alkynyl}G[5']p[p]_np[5']R_4^7G$.

For some alkynyl-derivatized cap analogs having the structure:

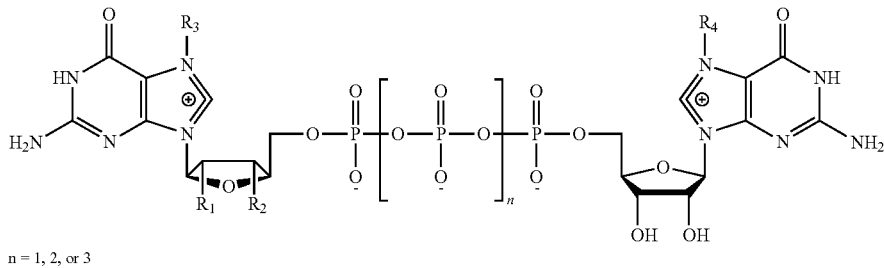

n = 1, 2, or 3

The term "azido" and "azide" are interchangeable and refer to a chemical compound that contains the group $N_3$.

The term "alkynyl" or "alkyne" are interchangeable and refer to a hydrocarbon having at least one terminal triple bond, i.e., the structure $(CH_2)_m C\equiv CH$ where m is 1 to 22, or 1, 2, 3, 4, 5, 6, 7, 8, 9, 10, 11, 12, 13, 14, 15, 16, 17, 18, 19, 20, 21, or 22. In particular, m is 1, 2, 3, 4, 5, or 6, or m is 1-6, or 1-10, or 1-12, for example. The term "alkynyl" may refer to a branched or an unbranched hydrocarbon group, or a substituted hydrocarbon chain, or as having further unsaturated bonds therein. In some embodiments, the alkynyl is n-propynyl, isopropynyl, n-butynyl, isobutynyl, t-butynyl, octynyl, decynyl and the like. The term "lower alkynyl" intends an alkynyl group of three to eight carbon atoms.

The term "moiety" and "group" are used interchangeably to refer to a portion of a molecule, typically having a particular functional or structural feature, e.g. a linking group (a portion of a molecule connecting two other portions of the molecule), or an ethyl moiety (a portion of a molecule with a structure closely related to ethane).

The terms "click" or "click chemistry," as used herein, refer to the Huisgen cycloaddition or the 1,3-dipolar cycloaddition between an azide and a terminal alkyne to form a 1,2,4-triazole.

The term "ARCA" or anti-reverse cap analog refers to a modified cap analog in which either the 3' —OH group or the 2' —OH group of the m7G is modified. This modification forces RNA polymerases to initiate transcription with the remaining —OH group in the G residue of the cap and thus synthesize RNA transcripts capped exclusively in the correct orientation. Therefore, use of the cap analog provided herein allows for synthesis of capped RNAs that are 100% functional in contrast to transcription reactions using traditional cap analogs where only half of the cap analog is incorporated in the correct orientation. Capped mRNAs provided herein $R_3$ and $R_4$ may be alkyl or arylalkyl. In some embodiments, the alkyl is methyl, ethyl, propyl, isopropyl, butyl or isobutyl. In other embodiments, the alkyl is methyl, ethyl, propyl or butyl. In some embodiments, the alkyl is a C1 to C12 alkyl. Representative examples of alkyl groups include methyl, ethyl, straight-chain, branched or cyclic isomers of propyl, butyl, pentyl, hexyl, heptyl, octyl, nonyl, and decyl. Alkyl groups may be substituted by at least one functional group. An arylalkyl group may be a moiety having a ring structure characteristic of benzene, naphthalene, phenanthrene, anthracene, and the like, i.e., either the 6-carbon ring of benzene or the condensed 6-carbon rings of the other aromatic derivatives. For example, an aryl group may be phenyl or naphthyl, and the term as used herein includes both unsubstituted aryls and substituted aryls.

A salt of an alkynyl-derivatized cap analog comprises a physiologically acceptable salt, such as a monovalent salt, for example, TEA, Tris, Li+, Na+ or ammonium, for example.

Figure 2:
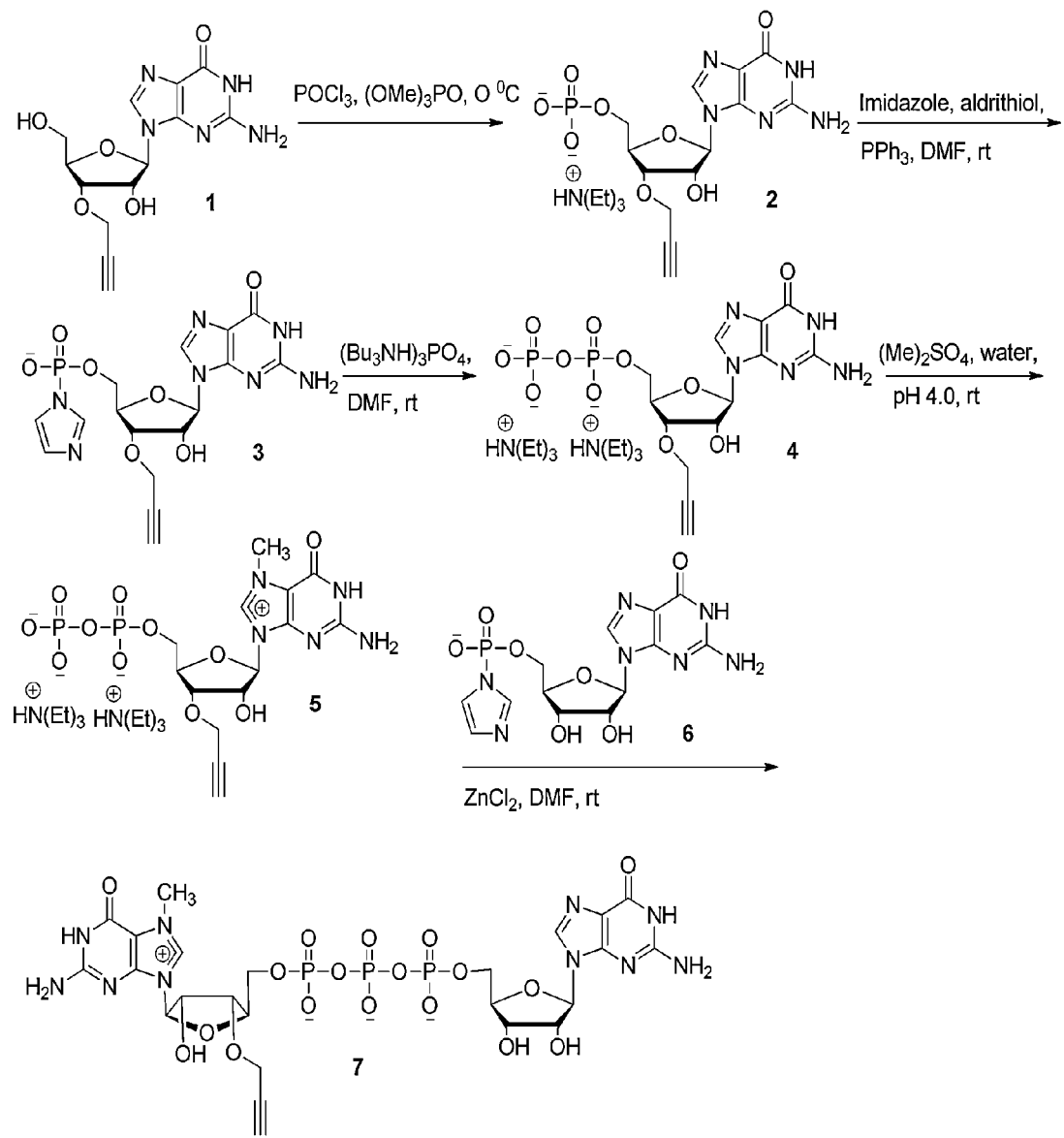
FIG. 2 provides a synthetic scheme for producing m$^{7,3'\text{-}O\text{-}propargyl}$GpppG 7, an alkynyl modified cap analog.

Alkynyl-derivatized cap analogs can be synthesized using the method shown in FIG. 2 where monophosphorylation of 3'-O-propargyl guanosine 1 was achieved using $POCl_3$ and trimethyl phosphate and resulted in 3'-O-propargyl GMP 2. The imidazolide reaction of 2 with imidazole, triphenyl phosphine, and aldrithiol resulted in the corresponding imidazolide salt, 3'-O-propargyl ImGMP 3. Next, the resulting imidazolide salt 3 was further phosphorylated using $(Bu_3NH)_3PO_4$ in the presence of zinc chloride as the catalyst and resulted in 3'-O-propargyl GDP 4. The methylation of 4 using dimethyl sulfate as the methylating agent under acidic conditions resulted in a highly regio selective N7 methylation product 5. Finally, the coupling reaction of $m^{7,3'\text{-}O\text{-}propargyl}GDP$ 5 with ImGMP 6 in the presence of zinc chloride as the catalyst resulted in $m^{7,3'\text{-}O\text{-}propargyl}G[5']ppp[5']G$ 7.

The term "alkynyl-modified capped RNA" refers to RNA having an alkynyl-derivatized cap covalently bonded thereto.

In some embodiments, the RNA is mRNA. In other embodiments, the RNA is non-coding RNA.

Reaction of an alkynyl-derivatized capped RNA with an azide-cleavable linker-reporter molecule/solid support yields a 1,4-disubstituted triazole-derivatized capped RNA-cleavable linker-reporter molecule/solid support conjugate. Cleavage of the linker results in a 1,4-substituted triazole-derivatized capped RNA-linker conjugate. The structure of the cleaved product varies depending on the structure of the linker and the method of cleavage. For example, cleavage of a linker containing a disulfide bond yields a sulfhydryl group at the end of the linker.

A linker can be a moiety that attaches a reporter or a solid support to alkynyl-derivatized capped RNA, which linker is cleavable under conditions that minimize damage to RNA. Alternatively, a linker can attach alkynyl-derivatized capped RNA to a solid support without the use of a reporter. The attachment is via the alkyne group on the alkynyl-derivatized capped RNA and an azide group on the reporter or the solid support.

A linker can be a cleavable linker. A "cleavable linker" is a linker that has one or more cleavable groups that may be broken by the result of a reaction or condition. The term "cleavable group" refers to a moiety that allows for release of a portion, e.g., a reporter moiety, carrier molecule or solid support, of a conjugate from the remainder of the conjugate by cleaving a bond linking the released moiety to the remainder of the conjugate. Such cleavage is either chemical in nature, or enzymatically mediated. Exemplary enzymatically cleavable groups include natural amino acids or peptide sequences that end with a natural amino acid. In addition to enzymatically cleavable groups, it is within the scope of the present invention to include one or more sites that are cleaved by the action of an agent other than an enzyme. Exemplary non-enzymatic cleavage agents include, but are not limited to, reducing agents (i.e., DTT or mercaptoethanol), acids, bases, light (e.g., nitrobenzyl derivatives, phenacyl groups, benzoin esters), heat, as well as other cleavable groups known in the art. Moreover a broad range of cleavable, bifunctional (both homo- and hetero-bifunctional) spacer arms are commercially available. An exemplary cleavable group, an ester, is cleavable group that may be cleaved by a reagent, e.g. sodium hydroxide, resulting in a carboxylate-containing fragment and a hydroxyl-containing product. Exemplary cleavable linkers include disulfide bonds and PC-linkers. Other linkers are discussed in the art, including U.S. Pat. No. 7,572,908, herein incorporated by reference in its entirety. A linker which has a disulfide linkage (S—S) can be cleaved by using dithiothreitol, e.g., a 50 mM solution of DTT. A linker which has photocleavable linkers (PC-Linkers) can be cleaved with certain UV lights.

The term "solid support," as used herein, refers to a material that is substantially insoluble in a selected solvent system, or which can be readily separated from a selected solvent system in which it is soluble. Solid supports useful in practicing the methods herein can include groups that are activated or capable of activation to allow selected one or more compounds described herein to be bound to the solid support. The material in the solid support may include a mineral or polymer, in which case the support is referred to as a "mineral or polymer support." Mineral or polymer supports include supports involving silica. In some embodiments, the silica is glass. Supports include, but are not limited to, beads, magnetic beads, columns and filters. In further embodiments, the mineral or polymer support is a glass fiber filter or column. In some embodiments, affinity chromatography can be used to isolate the capped and derivatized mRNAs from the uncapped mRNAs.

The term "reporter moiety" and "reporter" are interchangeable and refer to a moiety that is detectable. In some embodiments, the reporter is specifically bound by an affinity moiety. In some embodiments, the interaction of the reporter moiety and the affinity moiety provides for the isolation of 1,4-triazole-derivatized RNA that is attached to the reporter moiety. Examples include, but are not limited to biotin or iminobiotin and avidin or streptavidin. A sub-class of reporter moiety is an "epitope tag," which refers to a tag that is recognized and specifically bound by an antibody or an antigen-binding fragment thereof. Other reporters include, but are not limited to tags (with affinity partner), epitope tags (with antibody), and enzyme substrate (with enzyme). The reporter moiety can allow for attachment to a solid support for purification of the capped RNA. The reporter can be, for example, a dye, biotin, or a peptide. Examples of biotin molecules that can comprise the reporter moiety include $C_5$-$C_{20}$ O-biotin, SS-biotin, XX-biotin ((6-((6-((biotinoyl)amino)hexanoyl)amino)hexanoic acid succinimidyl ester), and NHS esters. For use in certain methods herein, the reporter includes an azide group to allow use in "click" technology.

Alkynyl-derivatized cap analogs provided herein are used for the synthesis of 5' alkynyl-derivatized capped RNA molecules in in vitro transcription reactions. Substitution of alkynyl-derivatized cap analogs for a portion of the GTP in a transcription reaction results in the incorporation of the alkynyl-derivatized cap structure into a corresponding fraction of the transcripts.

Figure 6:
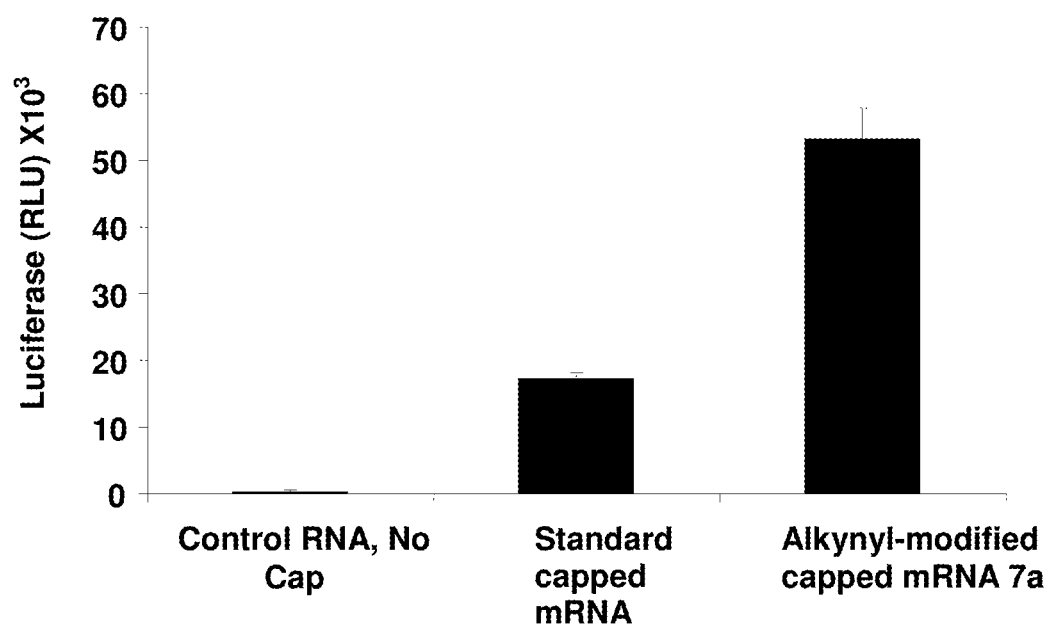

Alkynyl-derivatized capped mRNAs are generally translated more efficiently in reticulocyte lysate and wheat germ in vitro and in vivo translation systems as compared to standard capped mRNA. As provided by Example 4 below, luciferase activity was measured and revealed that the protein production using alkynyl-derivatized capped mRNA 7 (FIG. 2) was up to 3 fold higher than that using the standard cap ($m^7$GpppG-capped) mRNA (FIG. 6).

Embodiments herein provide for methods of using alkynyl-derivatized cap analogs to isolate mRNAs encoding specific genes to be transfected into eukaryotic cells or microinjected into cells or embryos to study the effect of translated product in the cell or embryo. Also included are methods of treating disease by transfecting such isolated mRNAs into cells isolated from a patient and thus expressing the specific protein encoded by the mRNAs.

The term "antigen presenting cell" (APC) refers to a cell displaying an antigen-MHC complex on its surface. The T-cell receptor of T-cells may recognize the antigen. Examples of APCs include without limitation dendritic cells, macrophages, B-cells, fibroblasts (skin), thymic epithelial cells, thyroid epithelial cells, glial cells (brain), pancreatic beta cells, and vascular endothelial cells (Steinman, R. M. and J. Banchereau, Nature 449, 419-426 (2007)) incorporated herein by reference).

Alkyne-derivatized cap analogs and, in particular, RNA coupled to an alkyne-derivatized cap analog, are/is detected or isolated by coupling the alkyne portion with an azide-derivatized reporter moiety, for example for detection, or an azide derivatized solid support for isolation, for example.

Azides and terminal alkynes undergo copper(I)-catalyzed azide-alkyne cycloaddition at room temperature. Such copper (I)-catalyzed azide-alkyne cycloadditions, also known as "click" chemistry, is a variant of the Huisgen 1,3-dipolar cycloaddition wherein organic azides and terminal alkynes react to give 1,4-disubstituted 1,2,3-triazoles. Examples of "click" chemistry reactions are described by Sharpless et al. U.S. Patent Application Publication No. 20050222427, published Oct. 6, 2005, PCT/US03/17311, U.S. Pat. Nos. 7,375,234 and 7,763,736 (which publications are herein incorporated by reference in their entirety); Lewis W G, et al., *Angewandte Chemie-Infl Ed,* 41:6, 1053; method reviewed in Kolb, H. C., et al, *Angew. Chem. Inst. Ed.* 2001, 40, 2004-2021, which developed reagents that react with each other in high yield and with few side reactions in a heteroatom linkage (as opposed to carbon-carbon bonds) in order to create libraries of chemical compounds.

The copper used as a catalyst for the "click" reaction used in some method embodiments described herein is in the Cu (I) reduction state. The sources of copper(I) used in such copper (I)-catalyzed azide-alkyne cycloadditions can be any cuprous salt including, but not limited to, cuprous halides such as cuprous bromide or cuprous iodide. However, this regioselective cycloaddition can also be conducted in the presence of a metal catalyst and a reducing agent. In certain embodiments, copper can be provided in the Cu (II) reduction state, for example, as a salt, such as but not limited to $Cu(NOs)_2$ $Cu(OAc)_2$ or $CuSO_4$, in the presence of a reducing agent wherein Cu(I) is formed in situ by the reduction of Cu(II). Such reducing agents include, but are not limited to, ascorbate, tris(2-carboxyethyl) phosphine (TCEP), 2,4,6-trichlorophenol (TCP), NADH, NADPH, thiosulfate, metallic copper, quinone, hydroquinone, vitamin $K_1$, glutathione, cysteine, 2-mercaptoethanol, dithiothreitol, $Fe^{2+}$, $Co^{2+}$, or an applied electric potential. In other embodiments, the reducing agents include metals selected from Al, Be, Co, Cr, Fe, Mg, Mn, Ni, Zn, Au, Ag, Hg, Cd, Zr, Ru, Fe, Co, Pt, Pd, Ni, Rh, and W.

The copper(I)-catalyzed azide-alkyne cycloadditions can be performed in water, an aqueous solution of a variety of solvents, including mixtures of water and (partially) miscible organic solvents including alcohols, dimethyl sulfoxide (DMSO), dimethyl formamide (DMF), tert-butanol (tBuOH) and acetone, or in organic solvents such as tetrahydrofuran.

Without limitation to any particular mechanism, copper in the Cu (I) state is a preferred catalyst for the copper(I)-catalyzed azide-alkyne cycloadditions, or "click" chemistry reactions, used in the methods described herein. Certain metal ions are unstable in aqueous solvents, by way of example Cu(I), therefore stabilizing ligands/chelators can be used to improve the reaction. In certain embodiments at least one copper chelator is used in the methods described herein, wherein such chelators binds copper in the Cu (I) state. In certain embodiments at least one copper chelator is used in the methods described herein, wherein such chelators binds copper in the Cu (II) state. In certain embodiments, the copper (I) chelator is a 1,10 phenanthro line-containing copper (I) chelator. Non-limiting examples of such phenanthro line-containing copper (I) chelators include, but are not limited to, bathophenanthroline disulfonic acid (4,7-diphenyl-1,10-phenanthroline disulfonic acid) and bathocuproine disulfonic acid (BCS; 2,9-dimethyl-4,7-diphenyl-1,10-phenanthroline disulfonate). Other chelators used in such methods include, but are not limited to, N-(2-acetamido)iminodiacetic acid (ADA), pyridine-2,6-dicarboxylic acid (PDA), S-carboxymethyl-L-cysteine (SCMC), trientine, tetra-ehylenepolyamine (TEPA), NNNN-tetrakis(2-pyridylmethyl)ethylenediamine (TPEN), EDTA, neocuproine, N-(2-acetamido)iminodiacetic acid (ADA), pyridine-2,6-dicarboxylic acid (PDA), S-carboxymethyl-L-cysteine (SCMC), tris-(benzyl-triazolylmethyl)amine (TBTA), or a derivative thereof. Most metal chelators, a wide variety of which are known in the chemical, biochemical, and medical arts, are known to chelate several metals, and thus metal chelators in general can be tested for their function in 1,3 cycloaddition reactions catalyzed by copper. In certain embodiments, histidine is used as a chelator, while in other embodiments glutathione is used as a chelator and a reducing agent.

The concentration of the reducing agents used in the "click" chemistry reaction described herein can be in the micromolar to millimolar range. In certain embodiments the concentration of the reducing agent is from about 100 micromolar to about 100 millimolar. In other embodiments the concentration of the reducing agent is from about 10 micromolar to about 10 millimolar. In other embodiments the concentration of the reducing agent is from about 1 micromolar to about 1 millimolar.

In certain embodiments, in the methods described herein using "click" chemistry, at least one copper chelator is added after copper(II) used in the reaction has been contacted with a reducing agent. In other embodiments, at least one copper chelator can be added immediately after contacting copper (II) with a reducing agent. In other embodiments, the copper chelator(s) is added between about five seconds and about twenty-four hours after copper(II) and a reducing agent have been combined in a reaction mixture. In other embodiments, at least one copper chelator can be added any time to a reaction mixture that includes copper(II) and a reducing agent, such as, by way of example only, immediately after contacting copper(II) and a reducing agent, or within about five minutes of contacting copper(II) and a reducing agent in the reaction mixture. In some embodiments, at least one copper chelator can be added between about five seconds and about one hour, between about one minute and about thirty minutes, between about five minutes and about one hour, between about thirty minutes and about two hours, between about one hour and about twenty-four hours, between about one hour and about five hours, between about two hours and about eight hours, after copper(II) and a reducing agent have been combined for use in a reaction mixture.

In other embodiments, one or more copper chelators can be added more than once to such "click" chemistry reactions. In embodiments in which more than one copper chelator is added to a reaction, two or more of the copper chelators can bind copper in the Cu (I) state or, one or more of the copper chelators can bind copper in the Cu (I) state and one or more additional chelators can bind copper in the Cu (II) state. In certain embodiments, one or more copper chelators can be added after the initial addition of a copper chelator to the "click" chemistry reaction. In certain embodiments, the one or more copper chelators added after the initial addition of a copper chelator to the reaction can be the same or different from a copper chelator added at an earlier time to the reaction.

The concentration of a copper chelator used in the "click" chemistry reaction described herein can be determined and optimized using methods well known in the art, including those disclosed herein using "click" chemistry to label nucleic acids followed by detecting such labeled nucleic acids to determine the efficiency of the labeling reaction and the integrity of the labeled nucleic acid(s). In certain embodiments, the chelator concentrations used in the methods described herein is in the micromolar to millimolar range, by way of example only, from 1 micromolar to 100 millimolar. In certain embodiments the chelator concentration is from about 10 micromolar to about 10 millimolar. In other embodiments the chelator concentration is from about 50 micromolar to about 10 millimolar. In other embodiments the chelator, can be provided in a solution that includes a water miscible solvent such as, alcohols, dimethyl sulfoxide (DMSO), dimethyl formamide (DMF), tert-butanol (tBuOH) and acetone. In other embodiments the chelator, can be provided in a solution that includes a solvent such as, for example, tetrahydrofuran, dimethyl sulfoxide (DMSO) or dimethylformamide (DMF).

While the methods used herein involve a copper catalyzed covalent reaction between an alkyne and an azide, it is envisioned that other methods using other catalysts (such as those using ruthenium) can also be used.

The "click" technology, as used herein, can result in isolation of up to 100% of capped mRNA. In some embodiments, the method can be used to isolate capped RNA to 80% to 100% purity, including but not limited to, 85%, 90%, 95%, and 100% purity. For example, 80% pure means that mRNA isolated using the "click" method results in less than 20% uncapped mRNA.

Figure 3:
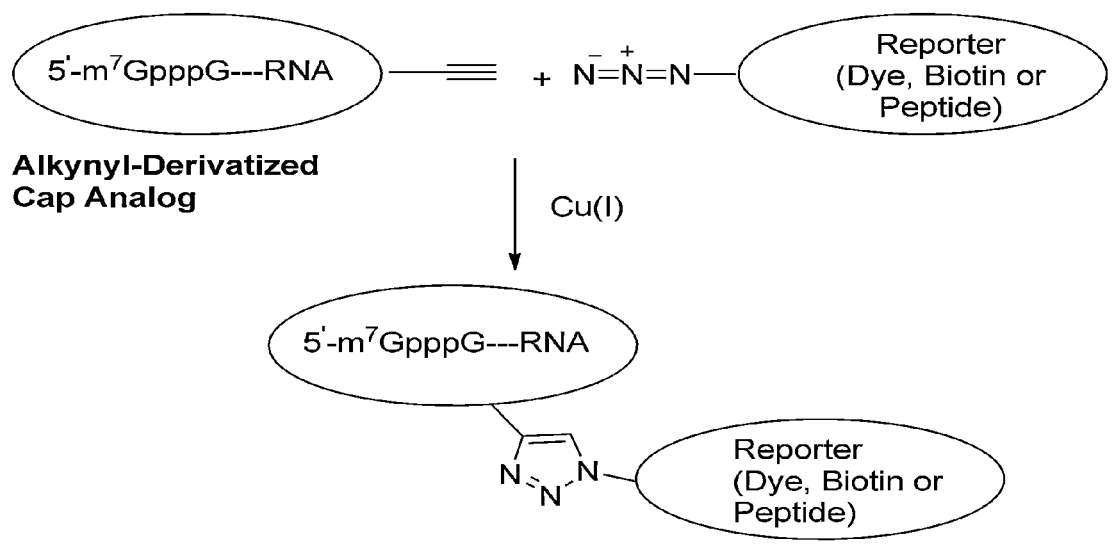
FIG. 3 provides a general scheme for coupling a RNA bearing an alkyne-modified cap analog to an entity bearing an azide group using "click" chemistry.

The scheme provided by FIG. 3 shows coupling of a RNA bearing an alkyne-modified cap analog to an entity bearing an azide group using "click" chemistry. In this case, the azide bearing entity contains a reporter moiety. In the presence of copper, a 1,4-disubstituted triazole derivative is formed containing capped RNA and the reporter. This conjugate, when contacted with an affinity column bearing an affinity molecule that binds to the reporter, allows for isolation of the RNA. When the RNA is mRNA, the derivatized mRNA can then be used in vitro in a cellular translation assay to produce a protein of interest. In certain embodiments, a reporter is not used and the alkynyl-modified capped mRNA binds directly to an azide-derivatized solid support.

Figure 5A:
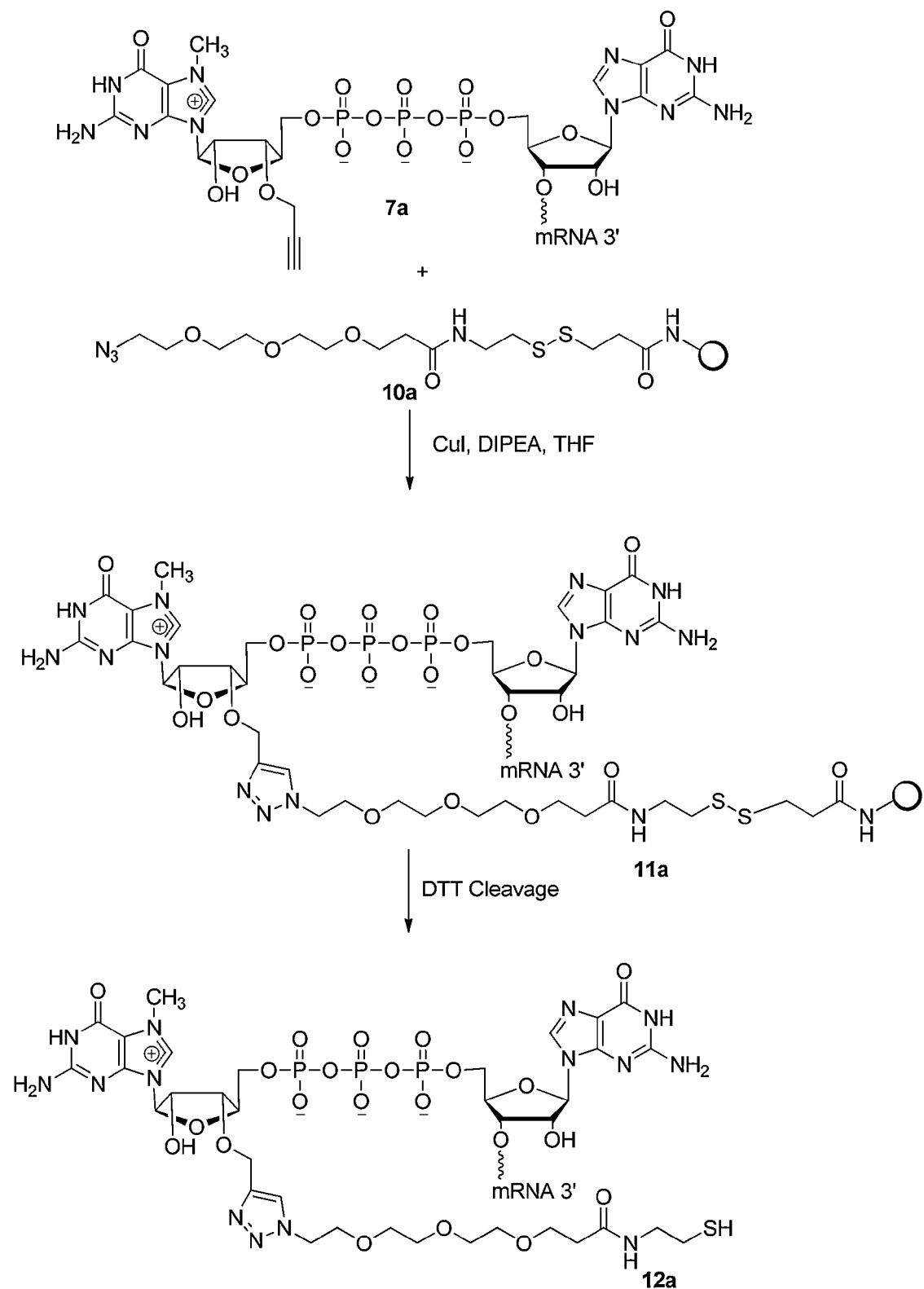
Figure 5B:
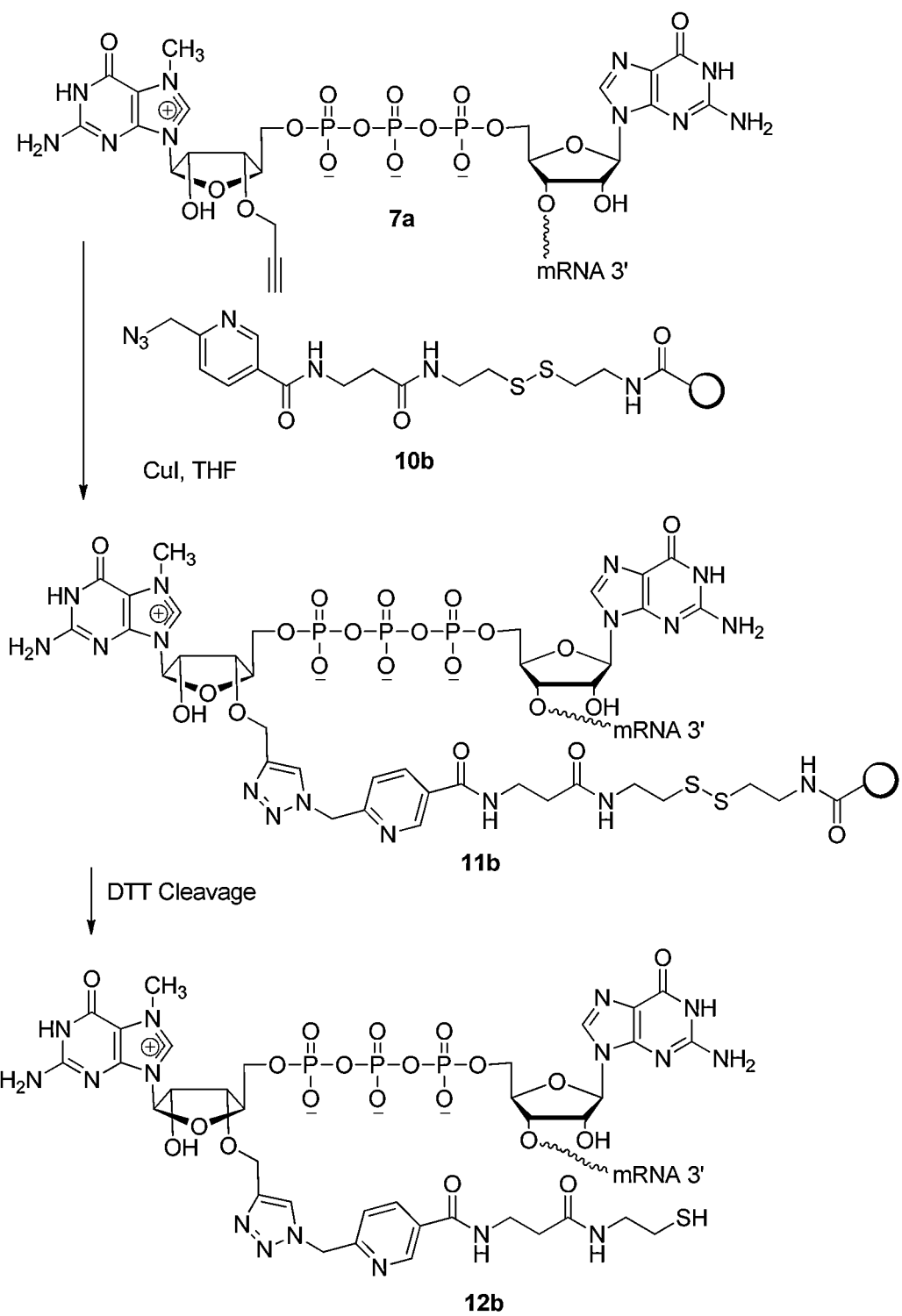
FIG. 5B provides a reaction scheme for coupling analog 7a with azide-derivatized solid support 10b to form reaction product 11b, which reaction product is cleaved by DTT to provide capped mRNA 12b.

As shown in FIG. 5A and FIG. 5B, in the presence of THF and CuI, the alkynyl-modified capped mRNA 7a binds to the azide derivatized solid support 10a or 10b, respectively. After washing, the solid supported conjugates 11a and 11b are cleaved with DTT to yield the 1,4-disubstituted triazole derivatives 12a and 12b, respectively.

Figure 7:
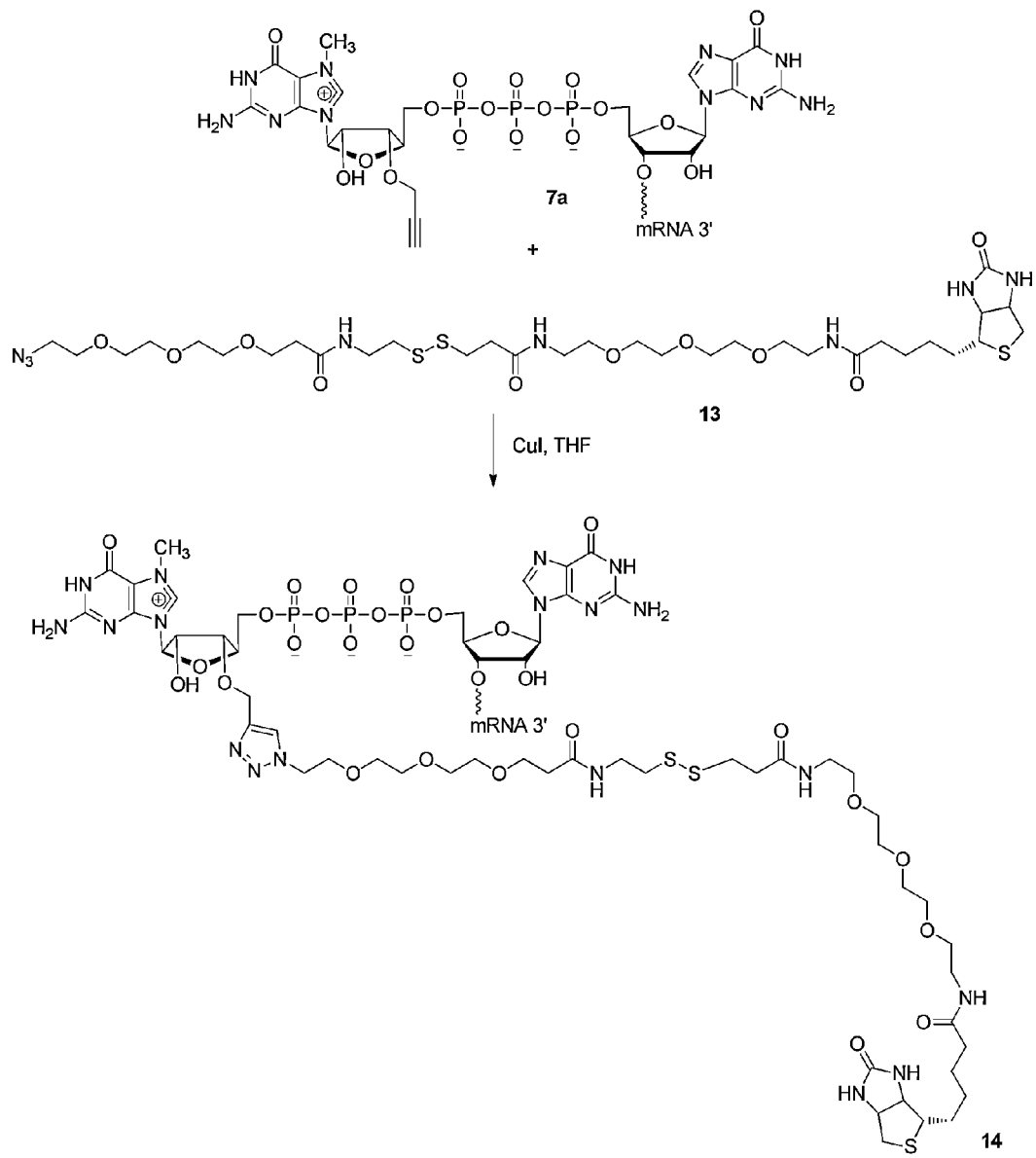
FIG. 7 provides a scheme for coupling alkynyl-modified capped mRNA 7a with an azido S—S-Biotin conjugate 13 to form streptavidin-detectable mRNA 14.

The scheme of FIG. 7 provides for binding of alkyne-derivatized capped mRNA 7a to biotin 13 via a disulfide cleavable linkage. The resulting 1,4-derivatized triazole conjugate 14 can be detected or, alternatively, detected and isolated using an affinity column bearing an avidin moiety that binds to the biotin to isolate the derivatized mRNA. The derivatized mRNA can be cleaved by cleaving the disulfide (S—S) bond of the biotin (e.g., using DTT). The resultant mRNA can then be used in vitro in a cellular translation assay to produce a protein of interest.

Figure 8A:
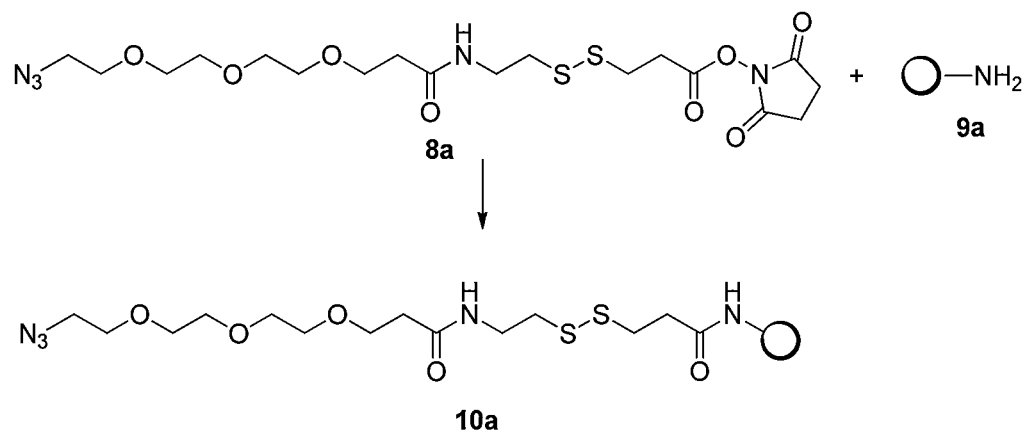
FIG. 8A and FIG. 8B provide schemes for preparation of solid-supports 10a and 10b
Figure 8B:
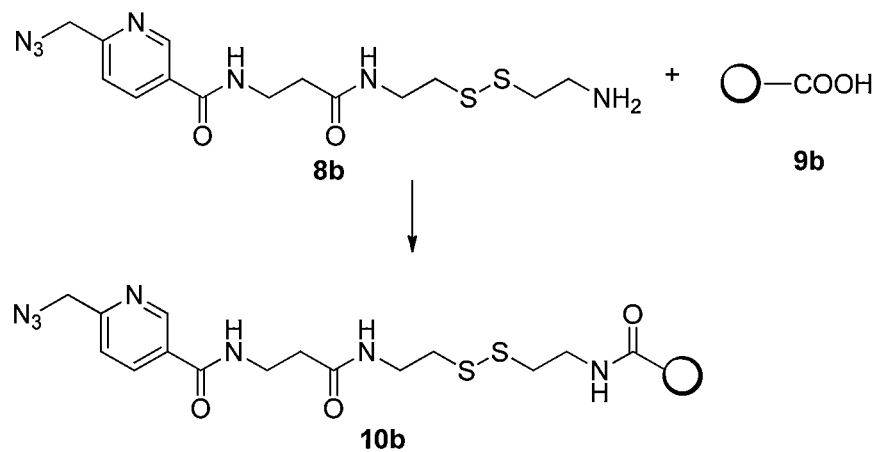

FIG. 8A and FIG. 8B provide azide containing cleavable linkers conjugated to a solid support or a reporter, 10a and 10b, for example. The solid support or reporter may have an amino moiety (9a) for reaction with an ester (8a) or a carboxy moiety (9b) for reaction with an amine (8b). Such linked solid supports or reporters can be used in methods herein for binding to alkyne-derivatized cap analogs or to alkyne-modified capped RNA. In one embodiment of FIG. 8A, a solid-supported S—S linker with an azide group 10a is produced by admixing a linker structure having a disulfide linker bearing an azide on one end and an ester on the other 8a with a solid support (e.g., a bead) bearing an amino group 9a in the presence of sodium bicarbonate as the base and THF as the solvent.

Cap analogs are used for the synthesis of 5' capped RNA molecules in transcription reactions. Substitution of cap analog for a portion of the GTP in a transcription reaction results in the incorporation of the cap structure into a corresponding fraction of the transcripts.

Transcription of RNA usually starts with a nucleoside triphosphate (usually a purine, A or G). When transcription occurs in vitro, it typically includes a phage RNA polymerase such as T7, T3 or SP6, a DNA template containing a phage polymerase promoter, nucleotides (ATP, GTP, CTP and UTP) and a buffer containing magnesium salt. The synthesis of capped RNA includes the incorporation of a cap (e.g., $m^7GpppG$) or a cap analog (such as those described herein) in the transcription reaction. Excess cap to GTP (e.g., 4:1) increases the opportunity that each transcript will have a 5' cap. The mMESSAGE mMACHINE® kit from Ambion (Ambion, Inc., Austin, Tex., a business of Applied Biosystems) recommends this ratio and will typically yield 80% capped RNA to 20% uncapped RNA, although total yields of total RNA are lower as GTP concentration becomes rate limiting as GTP is necessary for the elongation of the transcript.

Figure 4:
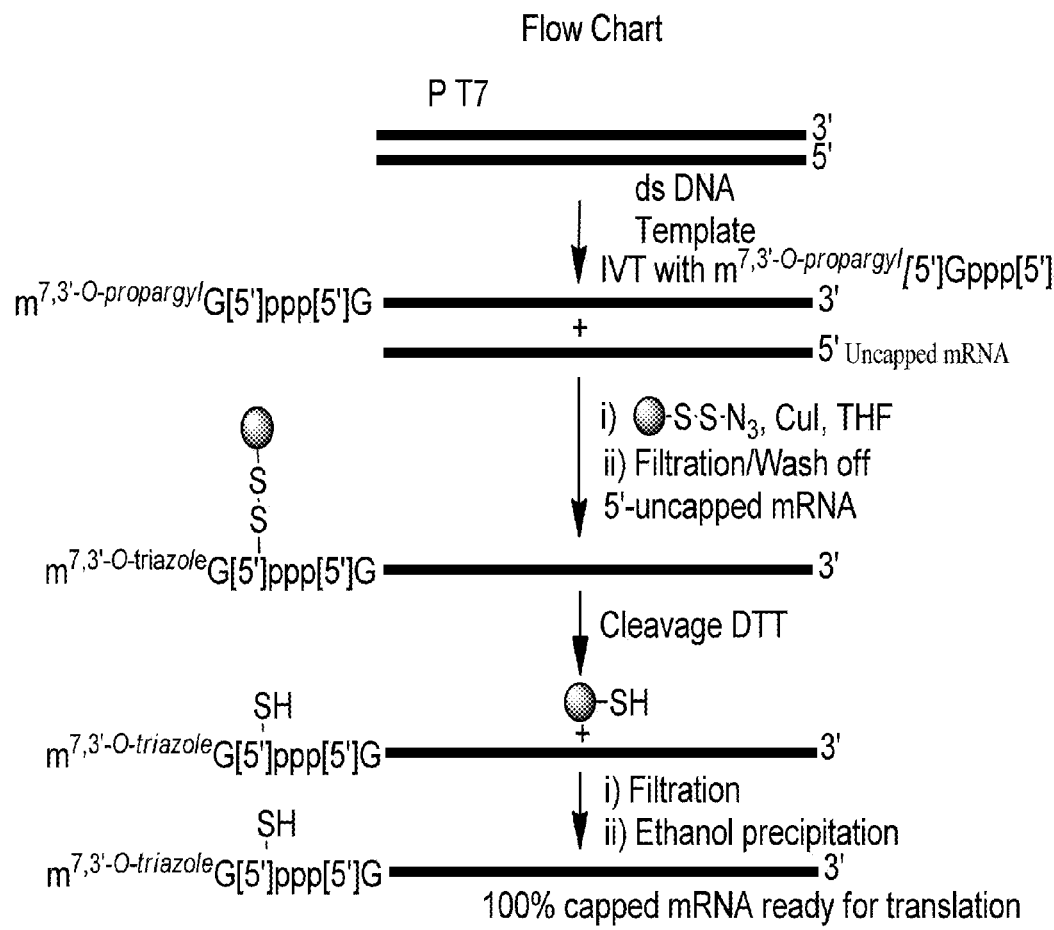
FIG. 4 provides a flow chart for in vitro transcription in the presence of an alkynyl-modified cap analog, coupling via "click" chemistry to an azide-derivatized solid support and isolation of capped mRNA.

In the scheme provided by FIG. 4, a flow chart for in vitro transcription in the presence of an alkynyl-modified cap analog is provided. Coupling of the alkyne-derivatized capped RNA via "click" chemistry to an azide-derivatized solid support containing a disulfide linker provides for isolation of triazole-derivatized capped RNA. The bead structure depicts a solid support or biotin or a reporter or a peptide. Uncapped RNA will not undergo the "click" reaction due to lack of an alkynyl-derivatized cap. After binding to the solid support, for example, the supernatant can be washed off or filtration can be performed to remove the uncapped RNA. The solid support with bound 5'-triazole-derivatized capped RNA can be washed and the RNA cleaved from the solid support with a substance that cleaves the cleavable linker (e.g., DTT for a disulfide). The cleaved 5'-triazole-derivatized RNAs can then be filtered and subjected to ethanol precipitation. Precipitated material will contain only 5'-capped RNA, and when the RNA is mRNA, the mRNA is ready for a translation assay (FIG. 4). The structure of the isolated RNA would vary depending on the linker, position and type of cleavable group.

Capped mRNAs are generally translated more efficiently in reticulocyte lysate and wheat germ in vitro translation systems. It is important that in vitro transcripts be capped for microinjection experiments because uncapped mRNAs are rapidly degraded. Cap analogs are also used as a highly specific inhibitor of the initiation step of protein synthesis.

The 5' cap structure enhances the translation of mRNA by helping to bind the eukaryotic ribosome and assuring recognition of the proper AUG initiator codon. This function may vary with the translation system and with the specific mRNA being synthesized. The consensus sequence 5'-GCCAC-CAUGG-3'(SEQ ID NO: 1), also known as the "Kozak" sequence, is considered to be the strongest ribosomal binding signal in eukaryotic mRNA. For efficient translation initiation, the key elements are the 5' G residue at the +1 position and the A residue at the 3' position of the mRNA.

The mRNA can be transfected into a cell to be translated intracellularly. Methods of transfection are known to those of skill in the art and include microinjection, electroporation, chemical treatments and the like. Cells for use in in vivo translation include any patient cell for which it is desired to express a protein of interest. Cells include hematopoietic cells (e.g., T cells, dendritic cells, macrophages, etc.), bone marrow cells, tissue culture cells, germ cells, and the like.

Compositions comprising alkynyl-modified capped RNA as described herein can be used for in vitro transcription, in vitro translation, and in vivo translation, for example. Current biotechnology efforts for in vitro, in cyto, and in vivo protein production will also benefit from these methods and compositions. Further, compositions provided herein are useful for therapeutic purposes. For example, the present technology may be useful for generating vaccines against infectious diseases or cancers. Alkyne-derivatized capped RNA can be used to produce non-infectious particles of Venezuelan Equine Encephalitis virus containing an RNA encoding immunogen. These non-replicating viral particles can be injected into humans where they can enter host cells. Once in the host cell, the viral particles dissociate and the mRNA encoding the immunogen is translated into protein. These proteins can induce an immune response. These types of vaccines are expected to be useful for human immunodeficiency virus (HIV), feline immunodeficiency virus, human papilloma virus type 16, tumors, lassa virus, Ebola virus, Marburg virus, anthrax toxin from *Bacillus anthraces*, and botulinum toxin. These vaccine strategies can require large quantities of capped RNA. The present methods facilitate such synthesis and subsequent purification of capped RNA so as to make these vaccines commercially feasible. As well, strategies to increase the percentage of full length capped RNA in a transcription reaction leading to a more homogenous product will be preferred in the vaccine industry as highly pure components are usually required for human use. In addition, researchers prefer to use products that are as pure as possible to minimize the number of variables in an experiment. As well, the purer the product, the more potent it is.

Another use of compositions described herein involves isolating dendritic cells (DCs) from a patient and then transfecting the dendritic cells with derivatized capped RNA as described herein encoding immunogen. The dendritic cells translate the derivatized capped RNA into at least one protein that induces an immune response against this protein.

In a small human study, immunotherapy with dendritic cells loaded with CEA capped RNA was shown to be safe and feasible for pancreatic cancer patients (Morse et al., *Int. J. Gastrointest. Cancer*, 32, 1-6 (2002)). It was also noted that introducing at least one single capped RNA species into immature dendritic cells induced a specific T-cell response (Heiser et al., *J. Clin. Invest*, 109, 409-417 (2002)). The cap analogs provided herein can be used for providing mRNAs for antigen delivery to DCs for the purpose of immunotherapy against cancer and infectious diseases.

Other uses include reprogramming differentiated cells to pluripotency and/or to re-program pluripotent cells using capped RNA described herein to specifically differentiate cell types by continuous transfection of specific derivatized-capped mRNAs over a time-period necessary for changing the cell differentiation.

The 1,4-disubstituted triazole derivatized capped RNA is expected to associate with biological targets through hydrogen bonding and dipole interactions that may play an important role in a drug discovery program. For example, the triazole product contains three nitrogen atoms in the ring that are capable of hydrogen bonding with biological targets.

An additional embodiment relates to the administration of a composition which generally comprises an active ingredient (e.g., alkynyl-modified capped RNAs or 1,4-disubstituted triazole capped RNAs) formulated with a pharmaceutically acceptable excipient. Excipients may include, for example, sugars, starches, celluloses, gums, and proteins. Various formulations are commonly known and are thoroughly discussed in the latest edition of Remington's Pharmaceutical Sciences (Maack Publishing, Easton Pa.). Such compositions may include novel cap analogs, antibodies to novel cap analogs, and mimetics, agonists, antagonists, or inhibitors of novel cap analogs.

In various embodiments, the compositions described herein, such as pharmaceutical compositions, may be administered by any number of routes including, but not limited to, oral, intravenous, intramuscular, intra-arterial, intramedullary, intrathecal, intraventricular, pulmonary, transdermal, subcutaneous, intraperitoneal, intranasal, enteral, topical, sublingual, or rectal means.

Embodiments of the present disclosure can be further understood in light of the following examples, which should not be construed as limiting the scope of the present disclosure in any way.

EXAMPLES

The following examples provide methods of producing alkynyl-derivatized cap analogs, alkynyl-modified capped RNA, 1,4-disubstituted triazole-derivatized capped RNA, as well as methods of isolation, and uses thereof.

Reagents: Reagents and solvents are used as such without further purification, unless otherwise stated. 3'-O-propargyl guanosine was purchased from Chemgenes, USA, $^1$H NMR and $^{31}$P NMR spectra were recorded in $D_2O$ on a Burker 400 MHz instrument. ESI mass spectra were recorded on an Applied Biosystems/Sciex API 150 model. HPLC was run on a waters 2996 (Waters Corporation) using anion exchange column. Ion exchange chromatography was performed in an AKTA purifier (Amersham Biosciences, GE Healthcare) using a DEAE Sepharose column. The gel shift assay was performed by using a pTri β actin template and the IVT reaction used linearized AmbLuc poly(A) DNA template and a MEGASCRIPT kit (Life Technologies Corporation). Radiation in the gel bands of interest was quantified by a phosphorimager (GE Healthcare). Purifications of the RNA from these transcription reactions were done by using the MEGACLEAR Kit (Life Technologies Corporation) as per manufacturer's protocol. Luminometer (POLARstar OPTIMA. BMG Labtech) in 96-well plates was used for the luciferase assay readings as per manufacturer's protocol.

Example 1

Synthesis of Alkynyl-Derivatized Cap Analog

An exemplary alkynyl-derivatized cap analog of FIG. 1G was synthesized using the scheme shown in FIG. 2. Bold numbers 1-7 designate structures 1-7 in FIG. 2. In brief, the monophosphorylation reaction of 3'-O-propargyl guanosine 1 was achieved using $POCl_3$ and trimethyl phosphate that furnished the corresponding 3'-O-propargyl GMP 2 in 85% yield. The imidazolide reaction of 2 with imidazole, triphenyl phosphine, and aldrithiol furnished the corresponding imidazolide salt, 3'-O-propargyl ImGMP 3 in 89% yield. Next, the resulting imidazolide salt 3 was further phosphorylated using $(Bu_3NH)_3PO_4$ in the presence of zinc chloride as the catalyst that furnished the corresponding 3'-O-propargyl GDP 4 in 71% yield. Notably, the methylation of 4 using dimethyl sulfate as the methylating agent under acidic conditions furnished a highly regioselective N7 methylation product 5 in 71% yield. Finally, the coupling reaction of m$^{7,3'\text{-}O\text{-}propargyl}$GDP 5 with ImGMP 6 in the presence of zinc chloride as the catalyst furnished m$^{7,3'\text{-}O\text{-}propargyl}$G[5']ppp[5']G 7 in 64% yield. Details are as follows.

Synthesis of 3'-O-propargyl GMP 2: To a stirred solution of $POCl_3$ (1.83 g, 12.12 mmol) and $(MeO)_3PO$ (25.0 mL) at 0° C. under an argon atmosphere, 3'-O-propargyl guanosine 1 (1.10 g, 4.05 mmol) was added and the reaction mixture was stirred for 4 h at 0° C. After 4 h, 50.0 mL water was added to the reaction mixture. The resulting reaction mixture was washed with dichloro methane (2×50 mL) to remove the phosphorylating agent. The collected aqueous solution was adjusted to pH 1.5 and allowed to stir at 4° C. for 15 h. After 15 h, the aqueous solution was adjusted to pH 6.5 and loaded on a DEAE Sepharose column The desired product was eluted using a linear gradient of 0-1M TEAB (triethyl ammonium bicarbonate, pH 7.5) and the fractions containing the product were pooled, evaporated and dried in a vacuum desiccator over phosphorous pentoxide to give a fine white powder 2 (Yield: 1.70 g, 85%).

Synthesis of 3'-O-propargyl ImGMP 3: To a stirred solution of 3'-O-propargyl GMP (1.50 g, 2.99 mmol) in 25 mL dry DMF, imidazole (0.97 g, 14.92 mmol), triphenyl phosphine (1.57 g, 5.99 mmol), aldrithiol (1.32 g, 6.00 mmol) and triethylamine (0.30 g, 2.97 mmol) were added. The reaction mixture was stirred under an argon atmosphere at room temperature for 16 h. To a solution of sodium perchlorate (1.50 g) in 100 mL acetone in a centrifuge tube at 0° C., the above reaction mixture was added slowly for 5 minutes. The resulting mixture was centrifuged and the supernatant liquid was removed. The solid was ground with a new portion of acetone (100 mL), cooled, and centrifuged again. This process was repeated two more times, and the resulting solid was dried in a vacuum desiccator over $P_2O_5$ to give a white powder 3 (Yield: 1.26 g, 89%).

Synthesis of 3'-O-propargyl GDP 4: To a stirred solution of 3'-O-propargyl ImGMP 3 (1.20 g, 2.67 mmol) and zinc chloride (1.81 g, 13.30 mmol) in 10.0 mL dry DMF, 15 mL of 1M tris(tributylammonium) phosphate in DMF was added under an argon atmosphere. The reaction mixture was stirred at room temperature for 5 h. After 5 h, the reaction mixture was diluted with 50.0 mL of water. The resulting reaction mixture was washed with ethyl acetate (2×50 mL) to remove phosphorylating agent. The collected aqueous solution was adjusted to pH 6.5 and loaded on a DEAE Sepharose column. The desired product was eluted using a linear gradient of 0-1M TEAB and the fractions containing the product were pooled, evaporated and dried in a vacuum desiccator over phosphorous pentoxide to give a fine white powder 4 (Yield 1.29 g, 71%).

Synthesis of m$^{7,3'\text{-}O\text{-}propargyl}$GDP 5: To a stirred solution of 3'-O-propargyl GDP 4 (1.10 g, 1.61 mmol) in 20.0 mL of water, acetic acid was added slowly to adjust the pH of the solution to 4.0. To this mixture, dimethyl sulfate (3.0 mL) was added drop-wise over a period of 30 min. and the reaction mixture was allowed to stir at room temperature for 5 h. As the methylation proceeded, the pH dropped down to around 2.0 and the pH was readjusted back to 4.0 using 1M NaOH solution. After 5 h, the reaction mixture was extracted with ethyl acetate (2×25 mL) to remove unreacted excess dimethyl sulfate. The collected aqueous solution was adjusted to pH 6.5 and loaded on a DEAE Sepharose column. The desired product was eluted using a linear gradient of 0-1M TEAB and the fractions containing the product were pooled, evaporated and dried in vacuum desiccator over phosphorous pentoxide to give a fine white powder 1 (Yield 0.79 g, 71%).

Synthesis of Reactant ImGMP 6: To a stirred solution of GMP TEA salt (5.00 g, 10.80 mmol) in 50 mL dry DMF, imidazole (3.51 g, 54.00 mmol), triphenyl phosphine (5.66 g, 21.60 mmol), aldrithiol (4.75 g, 21.59 mmol) and triethylamine (1.10 g, 10.89 mmol) were added. The reaction mixture was stirred under argon atmosphere at rt for 15 h. To a solution of sodium perchlorate (5.0 g) in 250 mL acetone in a centrifuge bottle at 0° C., the above reaction mixture was added slowly for 5 minutes. The resulting mixture was centrifuged and the supernatant liquid was removed. The solid was ground with a new portion of acetone (250 mL), cooled, and centrifuged again. This process was repeated for two more times, and the resulting solid was dried in a vacuum desiccator over $P_2O_5$ to give a white powder 6 (Yield: 4.46 g, 94%).

Synthesis of m$^{7,3'\text{-}O\text{-}propargyl}$[5']ppp[5']G 7: To a stirred solution of m$^{7,3'\text{-}O\text{-}propargyl}$GDP 5 (0.20 g, 0.29 mmol) and ImGMP 6 (0.12 g, 0.28 mmol) in 10.0 mL dry DMF, zinc chloride (0.19 g, 1.40 mmol) was added under an argon atmosphere and the reaction mixture was stirred at room temperature for 60 h. After 60 h, the reaction mixture was added to a solution of EDTA disodium (0.52 g, 1.40 mmol) in 100.0 mL of water at 0° C. The resulting aqueous solution was adjusted to pH 6.5 and loaded on a DEAE Sepharose column. The desired product was eluted using a linear gradient of 0-1M TEAB and the fractions containing the product were pooled, evaporated and concentrated to 10.0 mL TEA salt of 7. The resulting 10.0 mL was passed through a Strata-X-AW column and washed with 10.0 mL water followed by 10.0 mL MeOH. Then, the desired compound was eluted with 15.0 mL of $NH_4OH/MeOH/H_2O$ (2/25/73) and the collected solution was evaporated and dried to give a fine white powder 7. (Yield: 0.16 g, 64%).

Example 2

Analysis of Products by $^1H$ NMR and Mass Spectroscopy

The products from Example 1 were analyzed by $^1H$ NMR and Mass Spectroscopy as follows: $^1H$ NMR and $^{31}P$ NMR spectra were recorded in $D_2O$ on a Bruker 400 MHz instrument. $^1H$ was collected at 400.1446006 MHz and the $^{31}P$ was collected at 161.9968531, both using a QNP probe. Chemical shifts are reported in ppm, and signals are described as s (singlet), d (doublet), t(triplet), q (quartet), and m (multiplet). ESI mass was recorded on a Applied Biosystems/Sciex MDX API 150 model.

Data for $m^{7,3'\text{-}O\text{-}propargyl}G[5']ppp[5']G$ was as follows: $^1$H NMR ($D_2O$, 400 MHz) δ 7.99 (s, 1H), 5.87 (d, J=4.0 Hz, 1H), 5.79 (d, J=6.0 Hz, 1H), 4.68 (m, 2H), 4.49-4.21 (m, 10H), 4.06 (s, 3H), 2.91 (t, J=2.2 Hz, 1H); $^{31}$P NMR ($D_2O$, 162 MHz) δ −10.23 (d, J=20.7 Hz, 1P), −10.52 (d, J=19.4 Hz, 1P), −21.88 (t, J=20.1 Hz, 1P); MS (m/z): 839 [M+H]$^+$. The results show that the expected chemical structure 7 was obtained.

Example 3

Transcriptional Capping Efficiency of Standard Vs Alkyne-Derivatized CAP Analog The capping efficiencies of standard cap analog (Ambion, Life Technologies Corp.) and alkyne-derivatized CAP analog 7 (see Example 1) were tested using the following transcription and translation tests (see Example 4 for the translation test).

To analyze capping efficiency during transcription a Gel Shift Assay was used. The Gel shift assay was performed using the MAXISCRIPT kit (Life Technologies Corporation) by following the manufacturer's protocol. A typical 20 µL T7 RNA polymerase transcription reaction contained the following reagents at the final concentrations indicated: linearized pTri β actin vector template, 0.5 µg; ATP, 2 mM; GTP, 0.4 mM; compound standard cap analog and alkynyl-derivatized cap analog 7, 1.6 mM each in separate reactions; 10× reaction buffer, 4 µl T7 RNA polymerase, 50 units/µL; (α-$^{32}$P) ATP, 800 (Ci/mmol); and DEPC water. The control reaction was a normal in vitro transcription reaction, in which no cap analog was added. The transcription reactions were incubated at 37° C. for 2 h, after which the reaction mixtures were then applied to a 20% dPAGE gel. Radiation in the gel bands of interest was quantified by a phosphoroimager (GE Healthcare).

Due to the omission of CTP and UTP, only the 5' end was transcribed by T7 RNA polymerase, producing a transcript of six nucleotides in length. The resulting transcription products were analyzed by 20% denaturing polyacrylamide/8 M urea gel. The results from the gel shift assay showed that the standard cap had a capping efficiency of 73% while the alkynyl-derivatized cap analog 7 had a capping efficiency of 60%.

Example 4

Translation Efficiency of Standard Vs Alkyne-Derivatized CAP Analog

Alkynyl-derivatized capped mRNAs were produced in vitro for use in translation assays. T7 RNA polymerase transcription was performed using the MEGASCRIPT kit (Ambion, Life Technologies Corp.) in 20 µL final volume; the reaction contained the following reagents at the final concentrations indicated: linearized AmbLuc poly(A) DNA, 1.5 µg; 1× reaction buffer; ATP, UTP, and CTP, 7.5 mM each; GTP, 1.5 mM; alkynyl-modified cap analog 7 or m$^7$GpppG cap analog, 6.0 mM; and 50 units/µl of T7 RNA polymerase. The transcription reactions were incubated at 37° C. for 2 h. In order to hydrolyze the remaining plasmid DNA, 1 µL of TURBO DNase was added to the reaction mixture and further incubated at 37° C. for 15 min. Purification of transcription reactions was done by using the MEGAclear™ kit (Life Technologies Corp) as per manufacturer's protocol. The in vitro transcription results in a mixture of 5'analog-capped and uncapped mRNAs.

To determine the translational efficiency, the luciferase mRNA poly(A) product generated from the transcription reaction using a standard cap and the luciferase mRNA poly (A) product generated as described above using the alkyne-derivatized cap 7 were transfected separately into HeLa cells.

The HeLa cells (60,000/well in 24 well-plates) were seeded at least 12 h before transfection in growth medium without antibiotics. Capped RNA was prepared by mixing 600 ng of RNA, 2.5 µL of TFX-20™ (Promega), and 300 µL of serum-free DMEM in polystyrene tubes and incubated for 15 min at room temperature. After the incubation, media from the pre-plated HeLa cells was removed and 200 µL of the complex was added to each well. The plates were incubated for 1 h at 37° C., and then 1 mL of pre-warmed media with serum was added. The transfected plates were incubated at 37° C. for 16 h. Cells were harvested and lysed after 16 h. The cells were harvested by removing the media and adding 100 µL of 1× passive lysis buffer (Promega). The plate was mixed carefully to disrupt the cells and 10 µL of cell lysates from each transfection reactions were mixed with 100 µL of luciferase substrate (Promega) and measured immediately on a POLARstar OPTIMA Luminometer (BMG Labtech) in 96-well plates. The fold induction of luciferase protein data was normalized to the control reaction, i.e. no cap, mRNA poly(A) transfection results.

The translational luciferase data are provided in FIG. 6. The data reveal that the signal from protein produced from the luceriferase mRNA having alkyne-derivatized cap analog 7a was 3.1-fold greater than from mRNA having the standard cap analog. This result is comparable to the translational properties of the anti-reverse cap analogs of published U.S. Patent Appl'n No. 2010/0261231 published on Oct. 14, 2010.

Without being bound by theory, the translational properties of mRNA having alkyne-derivatized cap analog 7a over mRNA having the standard analog may be due to the formation of exclusive forward-capped mRNA poly(A) transcripts that lead to a homogeneous population of RNA molecules and/or due to the presence of the 3'-O-propargyl group, which might add to the stability of mRNA to accelerate the overall translational efficiency.

An advantage of the alkyne-derivatized cap analog derivatized mRNA is the ease of isolation of exclusively capped molecules as described below.

Example 5

Isolation of Capped mRNA Using the "Click" Reaction

In vitro transcription (IVT) results in 5'capped and uncapped mRNAs as a mixture. Since only the 5'capped mRNA has an alkynyl-derivatized cap, the capped molecules alone undergo the "click" reaction for purification of the capped mRNA. The "click" reaction is performed by using solid-supported azides with or without a cleavable linker arm, or biotin azide derivatives with or without a cleavable linker arm, or any reporter moiety derivatized with azide (e.g., dyes, heptanes) with or without a cleavable linker. The "click" reaction of the azide derivative and mRNA capped with an alkynyl-derivatized cap analog is performed in the presence of copper and tetrahydrofuran (THF). The reaction results in formation of a-1,2,3 triazole linker-mRNA product, while uncapped mRNA does not undergo the "click" reaction. The supernatant is then washed off or filtration is performed, so that the uncapped mRNA (that did not bind to the solid support) is washed away. The solid support having the bound 5'capped mRNA is washed three times with water (or up to ten times) and cleaved from the solid support (using TNF). Cleaved 5'capped mRNAs are filtered and subjected to ethanol precipitation. Precipitated material will contain only 5'capped mRNAs, which are ready for translation and/or transfection into a cell.

FIG. 5A and FIG. 5B provide schemes for isolation of 5'-capped mRNA using alkynyl-derivatized cap analog technology involving a solid-supported azide having different cleavable linkers. In each scheme, mRNA bearing an alkynyl-derivatized cap analog is admixed with a solid support bearing a cleavable linker and an azide group. In the presence of copper and THF, the "click" product is formed. The resulting alkynyl-derivatized capped mRNA attached to the solid support is then washed to remove unbound mRNA. The capped mRNA is cleaved from the solid support using DTT. The resulting capped mRNA can then be used in vitro in a cellular translation assay to produce a protein of interest, for example, or for in vivo use.

Example 6

Attachment of Derivatized Biotin to Alkynyl-Derivatized Cap Analog mRNA

FIG. 7 provides a scheme for coupling a mRNA having an alkynyl-modified cap analog 7a with azido S—S-Biotin conjugate 13. Admixing in the presence of copper and THF results in the "click" reaction to form S—S Biotin linked capped mRNA 14. The product is then run through an affinity column bearing a streptavidin or avidin moiety which binds to the biotin to isolate the capped mRNA (alternatively, it can be admixed with magnetic beads bearing a streptavidin or avidin affinity moiety). The capped mRNA 14 is cleaved by cleaving the disulfide (S—S) bond of the biotin (e.g., using DTT). The capped mRNA can then be used in vitro in a cellular translation assay to produce a protein of interest.

Example 7

Preparation of Azide-Derivatized Solid-Supports Having a Cleavable Linker

In each of FIG. 8A and FIG. 8B, a scheme is provided in which an azide-derivatized solid-support having a cleavable disulfide linkage is produced. For example, solid support 10a of FIG. 8A is produced by admixing a linker structure having a disulfide linker bearing an azide on one end and an ester on the other 8a with a solid support (e.g., a bead) bearing an amino group 9a in the presence of sodium bicarbonate as the base and THF as the solvent. The resulting solid support having an S—S linker and a terminal azide group can be used in methods of "click" chemistry to attach an alkynyl bearing capped mRNA. In one embodiment, this method includes use of a reporter or affinity moiety. The "clicked" and capped mRNA can be cleaved from the solid support by cleaving the S—S bond.

Solid support 10b of FIG. 8B is formed by reacting the amine of 8b with the carboxylated solid support 9b. Again, the "clicked" and capped mRNA can be cleaved from the solid support by cleaving the S—S bond.

Although the present disclosure is described with respect to certain embodiments and examples, various modifications may be made without departing from the spirit and scope of the invention.

What is claimed is:

1. A biological cell comprising a 1,4-disubstituted triazole-derivatized capped RNA.

2. A method of introducing an exogenous protein into a subject, comprising: transfecting the subject with a 1,4-disubstituted triazole-derivatized capped mRNA encoding the exogenous protein; and allowing intracellular translation to produce the exogenous protein.

3. The method of claim 2 wherein the subject is responsive to immunotherapy and the exogenous protein is an immunogen.

4. The method of claim 3, wherein the subject is a cell and the cell is an antigen presenting cell (APC).

* * * * *